US 9,988,357 B2

(12) United States Patent
Mani et al.

(10) Patent No.: US 9,988,357 B2
(45) Date of Patent: Jun. 5, 2018

(54) METHODS FOR PREPARATION OF QUINAZOLINE DERIVATIVES

(71) Applicant: Araxes Pharma LLC, San Diego, CA (US)

(72) Inventors: Neelakandha S. Mani, San Diego, CA (US); Brett D. Allison, San Diego, CA (US); Zachary S. Sales, Escondido, CA (US); Jimmy T. Liang, San Diego, CA (US); Xiaohu Deng, San Diego, CA (US); Liansheng Li, San Diego, CA (US); Yun Oliver Long, San Diego, CA (US); Yuan Liu, San Diego, CA (US); Pingda Ren, San Diego, CA (US)

(73) Assignee: Araxes Pharma LLC, La Jolla, CA (US)

( * ) Notice: Subject to any disclaimer, the term of this patent is extended or adjusted under 35 U.S.C. 154(b) by 0 days. days.

(21) Appl. No.: 15/373,832

(22) Filed: Dec. 9, 2016

(65) Prior Publication Data

US 2017/0190672 A1    Jul. 6, 2017

Related U.S. Application Data

(60) Provisional application No. 62/265,303, filed on Dec. 9, 2015.

(51) Int. Cl.
*C07D 239/94* (2006.01)
*C07D 239/86* (2006.01)

(52) U.S. Cl.
CPC ......... *C07D 239/94* (2013.01); *C07D 239/86* (2013.01)

(58) Field of Classification Search
CPC .................................................. C07D 239/94
See application file for complete search history.

(56) References Cited

U.S. PATENT DOCUMENTS

| | | |
|---|---|---|
| 3,702,849 A | 11/1972 | Cronin et al. |
| 3,752,660 A | 8/1973 | Little |
| 4,649,219 A | 3/1987 | Itoh et al. |
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Köster |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,017,696 A | 1/2000 | Heller |
| 6,043,031 A | 3/2000 | Köster et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |

(Continued)

FOREIGN PATENT DOCUMENTS

| | | |
|---|---|---|
| CN | 1267291 A | 9/2000 |
| EP | 0 606 046 A1 | 7/1994 |

(Continued)

OTHER PUBLICATIONS

Adibekian et al., "Optimization and characterization of a triazole urea dual inhibitor for lysophospholipase 1 (LYPLA1) and lysophospholipase 2 (LYPLA2)," *Probe Reports from the NIH Molecular Libraries Program*, 2011, 42 pages.

Al-Muhammed et al., "In-vivo studies on dexamethasone sodium phosphate liposomes," *J. Microencapsulation* 13(3):293-306, 1996.

Berge et al., "Pharmaceutical Salts," *Journal of Pharmaceutical Sciences* 66(1):1-19, 1977.

Cho et al., "An Unnatural Biopolymer," *Science* 261:1303-1305, Sep. 1993.

Chonn et al., "Recent advances in liposomal drug-delivery systems," *Current Opinion in Biotechnology* 6:698-708, 1995.

DeWitt et al., ""Diversomers": An approach to nonpeptide nonoligomeric chemical diversity," *Proc. Natl. Acad. Sci.* 90:6909-6913, Aug. 1993.

Furka et al., "General method for rapid synthesis of multicomponent peptide mixtures," *Int. J. Peptide Protein Res.* 37:487-493 1991.

(Continued)

*Primary Examiner* — Paul V Ward
(74) *Attorney, Agent, or Firm* — Seed IP Law Group LLP

(57) ABSTRACT

Methods for preparing compounds having the following structure (I):

(I)

or a pharmaceutically acceptable salt, stereoisomer, or tautomer thereof, wherein $R^1$, $R^{2a}$, $R^{2b}$, $R^{3a}$, $R^{3b}$, $R^{4a}$, $R^{4b}$ and $R^{4c}$, are as defined herein are provided. Related compounds and methods for making the same are also provided.

32 Claims, No Drawings

(56) References Cited

U.S. PATENT DOCUMENTS

| | | |
|---|---|---|
| 6,251,639 B1 | 6/2001 | Kurn |
| 6,903,118 B1 | 6/2005 | Biedermann et al. |
| 7,595,397 B2 | 9/2009 | Zindell et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,227,978 B2 | 1/2016 | Ren et al. |
| 9,376,559 B2 | 6/2016 | Holtcamp et al. |
| 9,745,319 B2 | 8/2017 | Ren et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2005/0012070 A1 | 1/2005 | Inoue et al. |
| 2005/0227997 A1 | 10/2005 | Noe et al. |
| 2008/0004285 A1 | 1/2008 | De Jonghe et al. |
| 2008/0004348 A1 | 1/2008 | Yous et al. |
| 2008/0039450 A1 | 2/2008 | Jensen et al. |
| 2009/0036430 A1 | 2/2009 | De Jonghe et al. |
| 2009/0054402 A1 | 2/2009 | Wang et al. |
| 2009/0124636 A1 | 5/2009 | Barber et al. |
| 2009/0298075 A1 | 12/2009 | Travers et al. |
| 2010/0331300 A1 | 12/2010 | Bian et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2013/0012489 A1 | 1/2013 | Mederski et al. |
| 2013/0029964 A1 | 1/2013 | Aoki et al. |
| 2013/0274252 A1 | 10/2013 | Pandey et al. |
| 2013/0302407 A1 | 11/2013 | Rao et al. |
| 2014/0288045 A1 | 9/2014 | Ren et al. |
| 2015/0087628 A1 | 3/2015 | Ostrem et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2016/0368930 A1 | 12/2016 | Ostrem et al. |
| 2017/0022184 A1 | 1/2017 | Li et al. |
| 2017/0131278 A1 | 5/2017 | Patricelli et al. |
| 2017/0197945 A1 | 7/2017 | Li et al. |

FOREIGN PATENT DOCUMENTS

| | | |
|---|---|---|
| EP | 0 780 386 A1 | 6/1997 |
| EP | 0 818 442 A2 | 1/1998 |
| EP | 0 931 788 A2 | 7/1999 |
| EP | 1 004 578 A1 | 5/2000 |
| GB | 939516 A1 | 10/1963 |
| JP | 59-163372 A | 9/1984 |
| JP | 2005-502623 A | 1/2005 |
| JP | 2007-16011 A | 1/2007 |
| JP | 2008-524154 A | 7/2008 |
| WO | 90/05719 A1 | 5/1990 |
| WO | 91/19735 A1 | 12/1991 |
| WO | 92/00091 A1 | 1/1992 |
| WO | 93/20242 A1 | 10/1993 |
| WO | 96/05309 A2 | 2/1996 |
| WO | 96/13262 A1 | 5/1996 |
| WO | 96/27583 A1 | 9/1996 |
| WO | 96/33172 A1 | 10/1996 |
| WO | 97/00271 A1 | 1/1997 |
| WO | 98/03516 A1 | 1/1998 |
| WO | 98/07697 A1 | 2/1998 |
| WO | 98/30566 A1 | 7/1998 |
| WO | 98/33496 A1 | 8/1998 |
| WO | 98/33768 A1 | 8/1998 |
| WO | 98/34915 A1 | 8/1998 |
| WO | 98/34918 A1 | 8/1998 |
| WO | 98/57948 A1 | 12/1998 |
| WO | 99/07675 A1 | 2/1999 |
| WO | 99/29667 A1 | 6/1999 |
| WO | 99/52889 A1 | 10/1999 |
| WO | 99/52910 A1 | 10/1999 |
| WO | 99/67641 A1 | 12/1999 |
| WO | 99/67641 A2 | 12/1999 |
| WO | 00/39587 A1 | 7/2000 |
| WO | 03/004480 A2 | 1/2003 |
| WO | 2004/074283 A1 | 9/2004 |
| WO | 2005/070891 A2 | 8/2005 |
| WO | 2005/082892 A2 | 9/2005 |
| WO | 2006/066948 A1 | 6/2006 |
| WO | 2006/135993 A1 | 12/2006 |
| WO | 2007/113226 A1 | 10/2007 |
| WO | 2007-144394 A2 | 12/2007 |
| WO | 2008/009078 A2 | 1/2008 |
| WO | 2010/027746 A2 | 3/2010 |
| WO | 2010/087399 A1 | 8/2010 |
| WO | 2010/121918 A1 | 10/2010 |
| WO | 2010/128918 A1 | 11/2010 |
| WO | 2011/031896 A2 | 3/2011 |
| WO | 2011/093524 A1 | 8/2011 |
| WO | 2011/148922 A1 | 12/2011 |
| WO | 2011/153553 A2 | 12/2011 |
| WO | 2012/016082 A1 | 2/2012 |
| WO | 2012/041872 A1 | 4/2012 |
| WO | 2012/054716 A1 | 4/2012 |
| WO | 2012/174489 A2 | 12/2012 |
| WO | 2013/064068 A1 | 5/2013 |
| WO | 2013/140148 A1 | 9/2013 |
| WO | 2013/155223 A1 | 10/2013 |
| WO | 2014/143659 A1 | 9/2014 |
| WO | 2014/152588 A1 | 9/2014 |
| WO | 2014/159837 A1 | 10/2014 |
| WO | 2014/201435 A1 | 12/2014 |
| WO | 2015/054572 A1 | 4/2015 |
| WO | 2015/144001 A1 | 10/2015 |
| WO | 2015/184349 A2 | 12/2015 |
| WO | 2016/044772 A1 | 3/2016 |
| WO | 2016/049565 A1 | 3/2016 |
| WO | 2016/049568 A1 | 3/2016 |
| WO | 2016049524 A1 | 3/2016 |
| WO | 2016/164675 A1 | 10/2016 |
| WO | 2016/168540 A1 | 10/2016 |
| WO | 2017/015562 A1 | 1/2017 |
| WO | 2017/070256 A2 | 4/2017 |

OTHER PUBLICATIONS

Hagihara et al., "Vinylogous Polypeptides: An Alternative Peptide Backbone," *J. Am. Chem. Soc.* 114(16):6568-6570, 1992.

Jones et al., "Increased frequency of the k-ras G12C mutation in MYH polyposis colorectal adenomas," *British Journal of Cancer* 90:1591-1593, 2004.

Li et al., "Methods and Compositions for Inhibition of Ras," U.S. Appl. No. 15/508,387, filed Mar. 2, 2017, 145 pages.

Liang et al., "Parallel Synthesis and Screening of a Solid Phase Carbohydrate Library," *Science* 274:1520-1522, Nov. 1996.

Lone et al., "A substrate-free activity-based protein profiling screen for the discovery of selective PREPL inhibitors," *J. Am Chem Soc.* 133(30):11665-11674, Aug. 2011. (20 pages).

Maurer et al., "Small-molecule ligands bind to a distinct pocket in Ras and inhibit SOS-mediated nucleotide exchange activity," *PNAS* 109(14):5299-5304, Apr. 2012.

Minto et al., "Pharmacokinetics and Pharmacodynamics of Nandrolone Esters in Oil Vehicle: Effects of Ester, Injection Site and Injection Volume," *The Journal of Pharmacology and Experimenial Thempeutics* 281(1);93-102, 1997.

Pathan et al., "Lead identification for the K-Ras protein: virtual screening and combinatorial fragment-based approaches," *OncoTargets and Therapy* 9:2575-2584, 2016.

Patricelli et al., "Selective Inhibition of Oncogenie KRAS Output with Small Molecules Targeting the Inactive State," *Cancer Discovery* 6(3)316-329, 2016.

Pautsch et al., "Crystal structure of the C3bot-RaIA complex reveals a novel type of action of a bacterial exoenzyme," *The EMBO Journal* 24:3670-3680, 2005.

(56) References Cited

OTHER PUBLICATIONS

Pinedo et al., "Aggressive combination therapy to cure patients with metastatic cancer," *The Lancet Oncology* 1:72-73, Oct. 2000.
PubChem Substance Record for SID 22405303, Mar. 5, 2007, CID 2579941 (MLS000416491), retreived from https://pubchem.ncbi.nlm.nih.gov/substance/22405303, on May 15, 2017, 7 pages.
PubChem Substance Record for SID 44253980, Dec. 5, 2007, CID 966800 (1-Benzoylpyrrolidine), retrieved from https://pubchem.ncbi.nlm.nih.gov/substance/44253980#section=Top on May 11, 2017, 5 pages.
Schubbert et al., "Biochemical Biology and Functional Characterization of Germ Line KRAS Mutations" *Molecular and Cellular Biology* 27(22):7765-7770, Nov. 2007.
Yan et al., "Discovery and characterization of small molecules that target the GRPase Ral," *Nature* 515:443-447, Nov. 2014. (15 pages).
Bachovchin et al., "Identification of selective inhibitors of uncharacterized enzymes by high-throughput screening with fluorescent activity-based probes," *Nature Biotechnology* 27(4):387-394, 2009. (11 pages).
CAS Registry No. 5530-21-2, "1-Propanone, 1[4-[2-(2-methoxy-4-propylphenoxy)acetyl]-1-piperazinyl]-," entered into STN Nov. 16, 1984, late updated Dec. 15, 2008, 6 pages.
Cox et al., "Drugging the undruggable RAS: Mission Possible?," *Nature Reviews Drug Discovery* 13:828-851, 2014.
Pardin et al., "Synthesis and evaluation of peptidic irreversible inhibitors of tissue transglutaminase," *Bioorganic & Medicinal Chemistry* 14:8379-8385, 2006.
Pubchem, "1-methoxy-3-tert-butyl-1H-isoindole," Compound Summary for CID 10375614, creation date Oct. 25, 2006, retrieved from https://pubchem.ncbi.nlm.nih.gov/compound/10375614, 9 pages.
Shima et al., "Discovery of Small-Molecule Ras Inhibitors that Display Antitumor Activity by Interfering with RAS•GTP-Effector Interaction," *The Enzymes* 34:1-23, 2013.
Sun et al., "Discovery of Small Molecules that Bind to K-Ras and Inhibit Sos-Mediated Activation," *Angew. Chem. Int. Ed.* 51:6140-6143, 2012.
Appel et al., "Supramolecular Cross-Linked Networks via Host-Guest Complexation with Cucurbit[8]uril," *J. Am. Chem. Soc.* 132(40):14251-14260, Jul. 2010.
Arkin et al., "Binding of small molecules to an adaptive protein—protein interface," *PNAS* 100(4):1603-1608, Feb. 2003.
Banker et al. (eds.), *Modern Pharmaceutics*, New York, Marcel Dekker, Inc., 1996, pp. 451 and 596. (3 pages).
Barbe et al., "Highly Chemoselective Metal-Free Reduction of Tertiary Amides," *J. Am. Chem. Soc.* 130:18-19, 2008.
Bégué et al., "Ions α-Cetocarbenium. Influence De La Structure Sur L'Evolution Des Ions α-Cetocyclohexylcarbenium," *Tetrahedron* 31(20):2205-2511, 1975. (English Abstract Only).
Chemcats Chemical Abstract, Accession No. 1301347730, Sep. 9, 2015, 2 pages.
Chemocare, "Taxol," retrieved from http://www.chemocare.com/chemotherapy/drug-info/Taxol.aspx on Feb. 22, 2017, 3 pages.
Choong et al., "Identification of Potent and Selective Small-Molecule Inhibitors of Caspase-3 through the Use of Extended Tethering and Structure-Based Drug Design," *J. Med. Chem.* 45:5005-5022, 2002.
Duncan et al., "N-Dialkylaminoalkybiphenylamines as Antimalarial and Atischistosomal Agents," *Journal of Medicinal Chemistry* 12:25-29, Jan. 1969.
Erlanson et al., "Site-directed ligand discovery," *Proc. Natl Acad. Sci. U.S.A.* 97(17):9367-9372, Aug. 2000.
Forbes et al., "Cosmic 2005," *British Journal of Cancer* 94:318-322, 2006.
Gorfe et al., "Mapping the Nucleotide and Isoform-Dependent Structural and Dynamical Features of Ras Proteins," *Structure* 16:885-896, Jun. 2008.

Hall et al., "The Effect of $Mg^{2+}$ on Guanine Nucleotide Exchange Rate of p21$N$-ras," *The Journal of Biological Chemistry* 261(24):10963-10965, 1986.
Hall et al., "The structural basis for the transition from Ras-GTP to Ras-GDP," *PNAS* 99(19):12138-12142, Sep. 2002.
Hardy et al., "Discovery of an allosteric site in the caspases," *PNAS* 101(34):12461-12466, Aug. 2004.
Hattori et al., "Neutralizing monoclonal antibody against ras oncogene product p21 which impairs guanine nucleotide exchange," *Mol. Cell. Biol.* 7(5):1999-2002, May 1987.
Ito et al., "Regional Polysterism in the GTP-Bound Form of the Human c-Ha-Ras Protein," *Biochemistry* 36(30):9109-1919, Jul. 1997.
Johnson et al., "The Chemistry of β-Bromopropionyl Isocyanate. I. Synthesis of 1-Aryldihydrouracils," *The Journal of Organic Chemistry* 24(9):1391-1392, Sep. 1959.
Jordan, "Tamoxifen: A most unlikely pioneering medicine," *Nature Reviews* 2:205-213, Mar. 2003.
Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinal Chemistry* 6(6):673-686, Jun. 1998.
Knochel et al., "Functionalization of heterocyclic compounds using polyfunctional magnesium and zinc reagents," Beilstein Journal of Organic Chemistry 7:1261-1277, 2011.
Kraulis et al., "Solution Structure and Dynamics of Ras p21-GDP Determined by Heteronuclear Three- amd Four-Dimensional NMR Spectroscopy," *Biochemistry* 33:3515-3531, 1994.
Kumar et al., "Synthesis of 3-Sulfonylamino Quinolines form 1-(2-Aminophenyl) Propargyl Alcohols through a Ag(I)-Catalyzed Hydroamination, (2 + 3) Cycloaddition, and an Unusual Strain-Driven Ring Expansion," *Organic Letters* 17(9):2226-2229, Apr. 2015.
Le Picard et al., "Design and Synthesis of Naphthalenic Derivatives as Potential Inhibitors of Hydroxyindole-O-methyltransferase," *Pharm. Pharmacol. Commun.* 5:183-188, 1999.
Lee et al., "The mutation spectrum revealed by paired genome sequences from a lung cancer patient," *Nature* 465:473-477, May 2010.
Lenzen et al., "[10] Analysis of Intrinsic and CDC25-Stimulated Guanine Nucleotide Exchange of p21$^{ras}$—Nucleotide Complexes by Fluorescence Measurements," Methods in Enzymology 255:95-109, 1995.
Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.
Loboda et al., "A gene expression signature of RAS pathway dependence predicts response to PI3K and RAS pathway inhibitors and expands the population of RAS pathway activated tumors," *BMC Medical Genomics* 3(26): 1-11, 2010.
Long, "Taxol: An important compound with an impressive structure," Organic and General Chemistry at Flathead Valley Community College, Sep. 10, 2011, retrieved from https://longscience.com/2011/09/10/taxol-an-organic-compound-you-should-know-about/ on Feb. 22, 2017, 4 pages.
Malani et al., "Synthesis, characterization and in vitro screening on bacterial, fungal and malarial strain of piprazinyl cyano biphenyl based compounds," *Bioorganic Chemistry* 51:16-23, 2013.
Margarit et al., "Structural Evidence for Feedback Activation by Ras•GTP of the Ras-Specific Nucleotide Exchange Factor SOS," *Cell* 112:685-695, Mar. 2003.
McMahon, "VEGF Receptor Signaling in Tumor Angiogenesis," *The Oncologist* 5(suppl. 1):3-10, 2000.
Milburn et al., "Molecular switch for signal transduction: structural differences between active and inactive forms of protooncogenic ras proteins," *Science* 247(4945):939-945, Feb. 1990.
Noe et al., "Selective Inhibition of Aggrecanase in Osteoarthritis .," Treatment," U.S. Appl. No. 60/148,464, filed Aug. 12, 1999, 92 pages.
Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 197.

(56) References Cited

OTHER PUBLICATIONS

Ostrem et al., "K-Ras(G12C) inhibitors allosterically control GTP affinity and effector interactions," *Nature 000*, 2013, 14 pages.
Pacold et al., "Crystal structure and functional analysis of Ras binding to its effector phosphoinositide 3-kinase gamma," *Cell* 103(6):931-943, Dec. 2000.
Palmioli et al., "First experimental identification of Ras-inhibitor binding interface using a water-soluble Ras ligand," *Bioorganic and Medicinal Chemistry* 19:4217-4222, 2009.
Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.
Pédeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.
Peri et al., "Arabinose-derived bicyclic amino acids: synthesis, conformational analysis and construction of an $\alpha_v\beta_3$-selective RGD peptide," *J. Am. Chem. Soc., Perkins Trans* 1(5):638-644, Feb. 2002.
Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.
Peri et al., "Synthesis of bicyclic sugar azido acids and their incorporation in cyclic peptides," *Chem. Commun.* 23:2303-2304, Jan. 2000.
Pinedo et al., "Translational Research: The Role of VEGF in Tumor Angiogenesis," *The Oncologist* 5(suppl. 1):1-2, 2000.
PubChem Compound, "(2S,6R)-hexahydrofuro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.
PubChem Compound, "(4-hydroxypiperidin-1-yl)-pyridin-4-ylmethanone: AC1LGBNJ," retrieved on Aug. 28, 2014, from http://pubchem.ncbi.nlm.nih.gov/summary/summary.cgi?cid=76837, Jul. 8, 2005, 3 pages.
PubChem Compound, "AKOS024742141," Nov. 27, 2010, retrieved from http://pubchem.ncbi.nim.nih.gov/compound/497021584#x304, CID 49702158, 12 pages.
PubChem Compound, "Compound Summary for CID 21765509: Molecular Formula $C_{18}H_{21}N_5O_8$," Dec. 5, 2007, rectried from http://pubchem.ncbi.nlm.nih.gov/compound/21765509, 4 pages.
PubChem Compound, "Compound Summary for CID 21765511: Molecular Formula $C_{18}H_{21}N_5O_8$," Dec. 5, 2007, retrieved from http://pubchem.ncbi.nlm.nih.gov/compound/21765511, 4 pages.
PubChem Compound, "Compound Summary for CID 60018735: Molecular Formula $C_{30}H_{30}O_{13}$," Aug. 20, 2012, retrieved from http://pubchem.ncbi.nlm.nih.gov/compound/60018735#section=Top, 1 page.
PubChem Compound, "Compound Summary for CID 72623693: AGN-PC-0D83J7," Jan. 9, 2014, retrieved from http://pubchem.ncbi.nlm.nih.gov/compound/72623693, 6 pages.
PubChem Compound, "Compound Summary for CID 9897840: Molecular Formula $C_{50}H_{46}O_{20}$," Oct. 25, 2006, retrieved from http://pubchem.ncbi.nlm.nih.gov/compound/9897840, 6 pages.
PubChem Compound, "SCHEMBL6674271," Dec. 1, 2012, retrieved from http://pubchem.ncbi.nim.nih.gov/compound/69861127#x304, CID 69861127, 12 pages.
PubChem Compound, "SCHEMBL6797439," Dec. 1, 2012, retrieved from http://pubchem.ncbi.nim.nih.gov/compound/69898605#x304, CID 69898605, 12 pages.
Rensland et al., "Substrate and Product Structural Requirements for Binding of Nucleotides to H-ras p21: The Mechanism of Discrimination between Guanosine and Adenosine Nucleotides," *Biochemistry* 34(2):593-599, 1995.
Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.
Singh et al., "A Gene Expression Signature Associated with "K-Ras Addiction" Reveals Regulators of EMT and Tumor Cell Survival," *Cancer Cell* 15:489-500, Jun. 2009.
Spiegel et al., "Small-molecule modulation of Ras signaling," *Nature Chemical Biology* 10:613-622, Aug. 2014.
Streuff et al., "First asymmetric aminohydroxylation of acrylamides," *Tetrahedron: Asymmetry* 16(20:3492-3496, Oct. 2005.
Sunaga et al., "Knockdown of Oncogenic KRAS in Non-Small Cell Lung Cancers Suppresses Tumor Growth and Sensitizes Tumor Cells to Targeted Therapy," *Molecular Cancer Therapeutics* 10(2):336-346, Feb. 2011.
Sydor et al., "Transient Kinetic Studies on the Interaction of Ras and the Ras-Binding Domain of c-Raf-1 Reveal Rapid Equilibration of the Complex," Biochemistry 37:14292-14299, 1998.
Taveras et al., "Ras Oncoprotein Inhibitors: The Discovery of Potent, Ras Nucleotide Exchange Inhibitors and the Structural Determination of a Drug-Protein Complex," *Bioorganic and Medicinal Chemistry* 5(1):125-133, 1997.
Tsubaki et al., "Reduction of metastasis, cell invasion, and adhesion in mouse osteosarcoma by YM529/ONO-5920-induced blockade of the Ras/MEK/ERK and Ras/PI3K/Akt pathway," *Toxicology and Applied Pharmacology* 259(3):402-410, Jan. 2012.
Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.
Vetter et al., "The Guanine Nucleotide-Binding Switch in Three Dimensions," *Science* 294(5545):1299-1304, Nov. 2001.
Vippagunta et al., "Crystalline solids," *Advanced Drug Delivery Reviews* 48:3-26, 2001.
Wolff, (ed.), *Burger's Medicinal Chemistry and Drug Discovery*, Fifth Edition, vol. 1: Principles and Practice, San Diego, California, John Wiley & Sons, 1994, pp. 975-977.
Wu et al., "Stereoselective synthesis of dioxabicycles from 1-C-allyl-2-O-benzyl-glycosides—An intramolecular cyclization between 2-O-benzyl oxygen and the allyl double bond," *Can. J. Chem.* 84(1):597-602, Jan. 2006.
Yang et al., "Fragment-Based Discovery of Nonpeptidic BACE-1 Inhibitors Using Tethering," *Biochemistry* 48:4488-4496, 2009.
Young et al., "Oncogenic and Wild-type Ras Play Divergent Roles in the Regulation of Mitogen-Activated Protein Kinase Signaling," *Cancer Discovery* 3(1):112-123, Jan. 2013.
Zenkl et al., "Sugar-Responsive Fluorescent Nanospheres," *Macromol. Biosci.* 8:146-152, 2008.

METHODS FOR PREPARATION OF QUINAZOLINE DERIVATIVES

BACKGROUND

Technical Field

The present invention generally relates to methods and compounds for preparing quinazoline and quinazoline derivatives using chemo and/or regioselective metalation reactions.

Background

The heterocyclyl fused ring scaffold of quinazoline has drawn interest in the field of pharmaceutical chemistry because of the diverse range of biological properties exhibited by compounds derived from such a substrate. Quinazoline scaffolds containing various substitution patterns are considered to be of important synthetic chemical as well as physiological importance. The range of biological activity exhibited by this class of compounds, and derivatives thereof, is wide and diverse, showing anticancer, antifungal, and antibacterial activity among many others. (Asif, M. Int. J. Med. Chem. 2014, 395637, 1-27). Accordingly, because of the complexity of functionalization and substitution patterns associated with pharmaceuticals, a synthetic method for selective functionalization of quinazoline scaffolds for use in synthesis of quinazoline derivatives is very valuable.

Given recent advancements in organometallic chemistry, functionalization via organometallic intermediates has become an important tool for synthesis of pharmaceutical products. Specifically, organozinc intermediates serve as an important synthetic species as they are compatible with a wide range of functional groups and afford desired products in high yields. Preparation of heteroaryl zinc intermediates is achieved by three general procedures; (1) insertion of zinc to heteroaryl iodides or bromides, (2) direct insertion of magnesium into heteroaryl halides with zinc (II) salts present, and (3) metalation with $(tmp)_2Zn \cdot 2MgCl_2 \cdot 2LiCl$. (Knochel, P.; Schade, M. A.; Bernhardt, S.; Manolikakes, G.; Metzger, A.; Piller, F. M.; Rohbogner, C. J.; Mosrin, M. Beilstein J. Org. Chem. 2011, 7, 1261-1277). Due to the low reactivity afforded by the carbon-zinc bond, the assistance of a transition metal catalyst is sometimes required to facilitate a reaction with an electrophile (i.e., via a Negishi cross-coupling; Wunderlich, S. H.; Knochel, P. Angew. Chem. Int. Ed. 2007, 46, 7685-7688).

Recently, heterocyclyl mixed metal bases have been developed for use in forming zinc intermediates via direct metalation. Those bases are related to the third procedure mentioned above (i.e., metalation with $(tmp)_2Zn \cdot 2MgCl_2 \cdot 2LiCl$) and have been reported to achieve chemo and regioselective metalations (Yus, M.; Foubelo, F. Handbook of Functionalized Organometallics; Knochel, P., Ed.; Wiley-VCH: Weinheim, Germany, 2005). However, this strategy has drawbacks. Specifically, only recently has this specific heterocyclyl mixed metal base been discovered so its synthetic methodology is relatively new and unpredictable (Knochel, P.; Schade, M. A.; Bernhardt, S.; Manolikakes, G.; Metzger, A.; Piller, F. M.; Rohbogner, C. J.; Mosrin, M. Beilstein J. Org. Chem. 2011, 7, 1261-1277). In some instances, high temperature and/or microwave irradiation is required to assist zinc metalation reactions that use $(tmp)_2Zn \cdot 2MgCl_2 \cdot 2LiCl$ (Wunderlich, S.; Knochel, P. Org. Lett. 2008, 10(20) 4705-4707). As of yet, there does not appear to be a way to accurately predict whether a specific scaffold will require high temperature or microwave irradiation to afford zincated synthetic intermediates in a regio-specific manner. Accordingly, although it appears the use of zincated intermediates tolerates most functional groups, certain substrates, sensitive to high temperatures or microwave irradiation, may complicate the use of this reaction strategy.

There have been some reported instances of organometallic chemistry relating to a quinazoline scaffolds, and derivatives thereof. One reported instance of organometallic chemistry related to selective lithiation of quinazoline. (Plé, N.; Turck, A.; Chapouland, V.; Quéguiner, G. Tetrahedron 1997, 53, 2871). While it would initially appear to be somewhat analogous to a zincation strategy, it is also known that aryl lithium species are highly reactive, and are not compatible in the presence of sensitive functional groups like esters or ketones (Yus, M.; Foubelo, F. Handbook of Functionalized Organometallics; Knochel, P., Ed.; Wiley-VCH: Weinheim, Germany, 2005; Vol. 1). As such, a pathway that makes use of a lithiated quinazoline intermediate would have only limited value in a synthetic strategy. Accordingly, lithiation of quinazolines would not be an ideal candidate for a scaffold containing incompatible functional groups like esters or ketones.

While various methods exist for preparing quinazoline compounds, there remains a need in the art for an improved methods and compounds for preparation of various functionalized quinazoline scaffolds. The present disclosure provides these and other related advantages.

BRIEF DESCRIPTION

Embodiments of the present invention provide methods and compounds for preparation of aryl or heteroaryl substituted quinazoline compounds. The provided methods are efficient and amenable to large scale manufacturing of the compounds, as well as smaller scale production for research purposes. The provided methods and compounds find utility in any number of applications, including preparation of compounds for treatment of various Kras-mediated cancers as described in PCT Pub. No: WO 2015/054572, the full disclosure of which is incorporated herein by reference.

Accordingly, in one embodiment, there is provided a method for preparing a compound having the following structure (I):

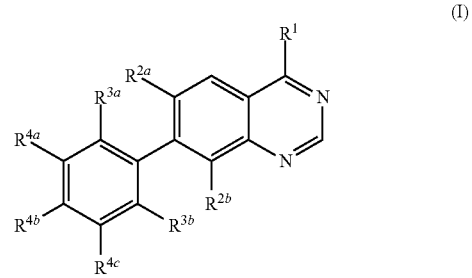

or a pharmaceutically acceptable salt or stereoisomer thereof, wherein $R^1$, $R^{2a}$, $R^{2b}$, $R^{3a}$, $R^{3b}$, $R^{4a}$, $R^{4b}$, and $R^{4c}$, are as defined herein, the method comprising preparing a mixture comprising a compound of structure (II) and a compound of structure (III), the compounds of structure (II) and (III) having the following structures, respectively:

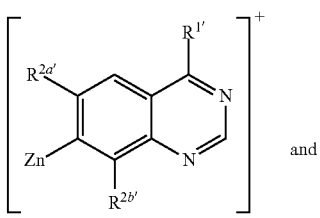

(II)

and

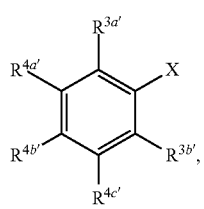

(III)

or a salt thereof, wherein $R^{1'}$, $R^{2a'}$, $R^{2b'}$, $R^{3a'}$, $R^{3b'}$, $R^{4a'}$, $R^{4b'}$, $R^{4c'}$ and X are as defined herein, thereby forming a carbon-carbon bond between the carbon bearing the Zn moiety on compound (II) and the carbon bearing the X moiety on compound (III).

Other embodiments provide compounds useful for preparation of compounds of structure (I), for example in some embodiments is provided a compound having the following structure (II):

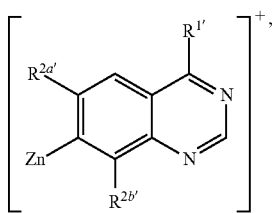

(II)

or a salt thereof, wherein $R^{1'}$, $R^{2a'}$ and $R^{2b'}$ are as defined herein.

Still other embodiments provide different compounds having the following structure (V):

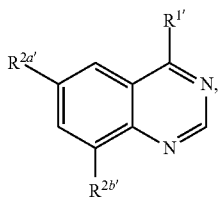

(V)

or a salt thereof, wherein $R^{1'}$, $R^{2a'}$ and $R^{2b'}$ are as defined herein.

These and other aspects of the invention will be apparent upon reference to the following detailed description. To this end, various references are set forth herein which describe, in more detail, certain background information, procedures, compounds and/or compositions and are each hereby incorporated by reference in their entirety.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form of "a", "an" and "the" include plural references unless the context clearly dictates otherwise.

"Halo" refers to chloro, fluoro, bromo or iodo.

"Hydroxy" or "hydroxyl" refers to the —OH radical.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). Unless stated otherwise specifically in the specification, an alkyl group is optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group is optionally substituted.

"Aryl" refers to a hydrocarbon ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Carbocyclyl" refers to a stable, aromatic or non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is attached to the rest of the molecule by a single bond. Carbocyclyls include aryl and cycloalkyl groups. Unless otherwise stated specifically in the specification, a carbocyclyl group is optionally substituted.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Heterocyclyl" or "heterocyclyl ring" refers to a stable 3- to 18-membered aromatic or non-aromatic ring radical which consists of two to twelve carbon atoms and from one to six heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such non-aromatic heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification. "Unless stated otherwise specifically in the specification, a heterocyclyl group is optionally substituted.

"Heteroaryl" refers to a heterocyclyl group having a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group is optionally substituted.

"Mixed metal heterocyclyl base" refers to a reagent comprising a basic heterocyclyl moiety and two or more metals. The reagent contains anions such that the overall complex is charge neutral. Examples of metals include, but are not limited to zinc, magnesium, and lithium. Examples of heterocycles include those defined herein. Examples of anions include, but are not limited to chloride. Examples of a "mixed metal heterocyclyl base" include, but are not limited to 2,2,6,6-Bis(tetramethylpiperidine)zinc, magnesium chloride, lithium chloride complex, referred to herein as $(tmp)_2Zn.2MgCl_2.2LiCl$.

Various catalysts and precatalysts are useful in certain embodiments of the invention. In some embodiments, a palladium catalyst or precatalyst is used, for example a homogenous palladium catalyst or precatalyst. One of ordinary skill in the art can determine appropriate palladium-based catalysts or precatalyst useful to implement embodiments of the invention. The palladium catalysts and/or precatalysts can be selected from those known in the art or derived by one of ordinary skill in the art. In one embodiment the precatalyst is "CPhos $3^{rd}$ generation," which has the following structure:

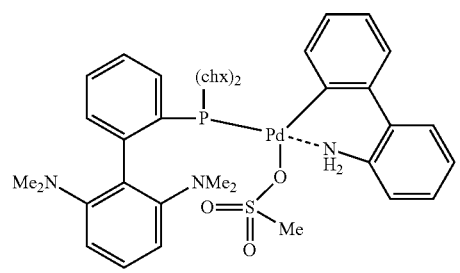

A "protected hydroxyl" group is an oxygen moiety bearing a functionality, which can be removed to reveal a free hydroxy. One of ordinary skill in the can derive appropriate protected hydroxyl groups for use in the embodiments of the invention.

A "non-acidic substituent" is a substituent having no hydrogen atoms sufficiently acidic to be deprotonated in the presence of the mixed metal, heterocyclic bases employed in various embodiments of the invention. "Sufficiently acidic" means, at equilibrium in the presence of the mixed metal, heterocyclic bases, the hydrogen atoms will at most be 5% or less than 1% deprotonated.

The term "substituted" used herein means any of the above groups (e.g., alkyl, alkoxy, aryl, carbocyclyl, cycloalkyl, haloalkyl, heterocyclyl and/or heteroaryl) wherein at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Accordingly, certain embodiments of the methods comprise enriching a racemic mixture to obtain an enriched or substantially pure (e.g., greater than 95% or greater than 99%) enantiomer. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the invention may exist as mixtures of atropisomers or purified or enriched for the presence of one atropisomer. Non-limiting examples of compounds which exist as atropisomers include the following compounds:

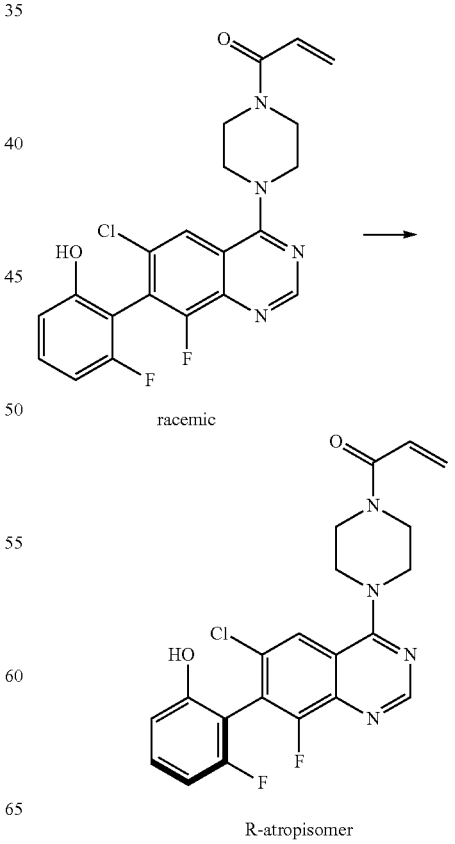

-continued

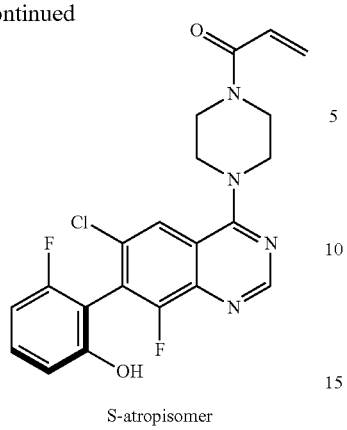

S-atropisomer

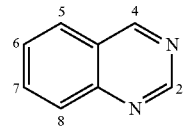

quinazoline

Accordingly, in various embodiments is provided a method for preparing a compound having the following structure (I):

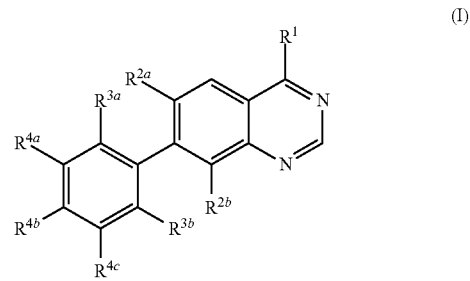

or a pharmaceutically acceptable salt, tautomer, prodrug or stereoisomer thereof, wherein:

$R^1$ is a non-hydrogen substituent;

$R^{2a}$ and $R^{2b}$ are each independently halo, hydroxyl, protected hydroxyl, $C_1$-$C_6$ alkyl, $C_1$-$C_6$ haloalkyl or $C_1$-$C_6$ alkoxy;

$R^{3a}$ and $R^{3b}$ are each independently halo, hydroxyl, protected hydroxyl, $C_1$-$C_6$ alkyl, $C_1$-$C_6$ haloalkyl or $C_1$-$C_6$ alkoxy; or $R^{3a}$ joins with $R^{4a}$ to form a carbocyclyl or heterocyclic ring, and $R^{3b}$ is halo, hydroxyl, protected hydroxyl, $C_1$-$C_6$ alkyl, $C_1$-$C_6$ haloalkyl or $C_1$-$C_6$ alkoxy; and $R^{4a}$, $R^{4b}$ and $R^{4c}$ are each independently H or a non-hydrogen substituent; or $R^{4a}$ joins with $R^{3a}$ to form a carbocyclyl or heterocyclic ring, and $R^{4b}$ and $R^{4c}$ are each independently H or a non-hydrogen substituent;

wherein the method comprises preparing a mixture comprising a compound of structure (II) and a compound of structure (III), the compounds of structure (II) and (III) having the following structures, respectively:

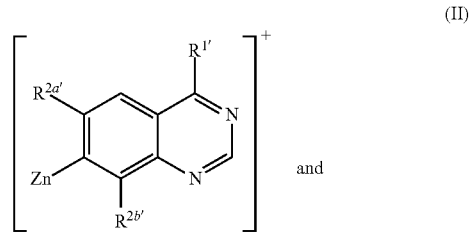

and

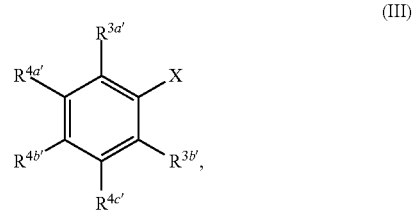

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 14.0 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Embodiments of the invention are directed to preparation of various compounds comprising a quinazoline moiety. The presently described metalation reactions for forming a carbon-carbon bond between a quinazoline core and an aryl or heteroaryl substituent have not previously been reported. Surprisingly, the present inventors have discovered that the disclosed metalations (and subsequent carbon-carbon bond formation) proceeds in a regiospecific manner at carbon 7 of the quinazoline (see below structure), although other metalation sites are available (e.g., carbons 2 and 5). Further, and in contrast to other methods for forming the desired carbon-carbon bond (e.g., Suzuki coupling), the present inventors have discovered that the present metalation reactions are highly efficient despite steric hindrance at the site of carbon-carbon bond formation. For example, in certain embodiments a carbon-carbon bond is formed between carbon 7 of a quinazoline and carbon 1 of an aryl or heteroaryl moiety (e.g., phenyl), while the quinazoline has non-hydrogen substituents at the 6 and 7 positions, and the aryl or heteroaryl has non-hydrogen substituents at the 2 and 6 positions (i.e., both carbons adjacent the newly formed carbon-carbon bond are substituted with non-hydrogen substituents).

or a salt thereof, wherein:
R$^{1'}$ is a non-hydrogen, non-acidic substituent;
R$^{2a'}$ and R$^{2b'}$ are each independently halo, protected hydroxyl, C$_1$-C$_6$ alkyl, C$_1$-C$_6$ haloalkyl or C$_1$-C$_6$ alkoxy;
R$^{3a'}$ and R$^{3b'}$ are each independently halo, protected hydroxyl, C$_1$-C$_6$ alkyl, C$_1$-C$_6$ haloalkyl or C$_1$-C$_6$ alkoxy; or R$^{3a'}$ joins with R$^{4a'}$ to form a carbocyclyl or heterocyclic ring, and R$^{3b'}$ is halo, protected hydroxyl, C$_1$-C$_6$ alkyl, C$_1$-C$_6$ haloalkyl or C$_1$-C$_6$ alkoxy;
R$^{4a'}$, R$^{4b'}$ and R$^{4c'}$ are each independently H or a non-hydrogen substituent; or R$^{4a'}$ joins with R$^{3a'}$ to form a carbocyclyl or heterocyclic ring, and R$^{4b'}$ and R$^{4c'}$ are each independently H or a non-hydrogen substituent; and
X is a leaving group,
thereby forming a carbon-carbon bond between the carbon bearing the Zn moiety on compound (II) and the carbon bearing the X moiety on compound (III).

For ease of illustration, the compound of structure (II) is often illustrated in a cationic form throughout the description of the methods and compounds herein. It will be apparent to one of ordinary skill in the art that the compound of structure (II) will be associated with a counter ion, and the compounds of structure (II) in their associated form are also included within the scope of the methods and compounds described herein. For example, the compounds of structure (II) may be associated with a counter ion and represented as follows (II'):

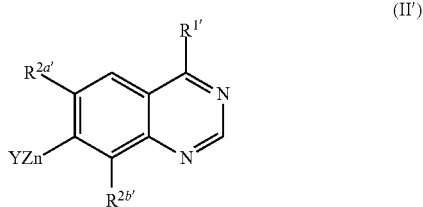

(II')

wherein Y is a counter ion, such as halogen (e.g., Cl, Br or I).

In other aspects, the compound of structure (II) forms a pseudo-dimer and can be represented as follows (II"):

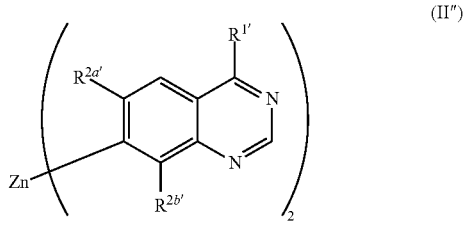

(II")

In some embodiments, the compound of structure (II) is prepared by reaction of a mixed-metal, heterocyclic base with a compound having the following structure (IV):

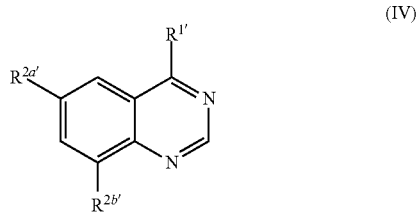

(IV)

In various other embodiments, the heterocyclyl base comprises Zn, Mg and/or Li.

In some different embodiments, the mixed metal, heterocyclic base comprises a piperidinyl heterocycle. For example, in some embodiments the mixed metal, heterocyclic base comprises a 2,2,6,6-Bis(tetramethylpiperidine) zinc, magnesium chloride, lithium chloride complex ((tmp)$_2$Zn.2MgCl$_2$.2LiCl).

In other embodiments, the mixture comprising a compound of structure (II) and a compound of structure (III) further comprises a metal catalyst or metal precatalyst. For example, in some embodiments the metal is palladium. In other embodiments, the metal precatalyst is CPhos 3$^{rd}$ generation.

Various different solvents can be used for the disclosed transformations. In some embodiments, the mixture comprising a compound of structure (II) and a compound of structure (III) comprises a polar, aprotic solvent. For example, in some embodiments the solvent is tetrahydrofuran.

In some other different embodiments, R$^1$ and R$^{1'}$ are each independently C$_1$-C$_6$ alkyl, carbocyclyl or heterocyclyl. In some exemplary embodiments, R$^1$ and R$^{1'}$ are each independently heterocyclyl. For example, in some embodiments the heterocyclyl is piperazinyl. In some more embodiments, R$^1$ and R$^{1'}$ each have the following structure:

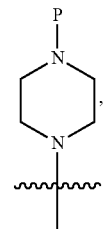

wherein P is a nitrogen protecting group, such as butyloxycarbonyl (Boc).

In other embodiments, R$^{2a}$ and R$^{2b}$ are each independently halo. In some other embodiments, R$^{2a'}$ and R$^{2b'}$ are each independently halo.

In some other different embodiments, R$^{3a}$ and R$^{3n}$ are each independently halo, hydroxyl or C$_1$-C$_6$ alkoxy, and in other embodiments, R$^{3a'}$ and R$^{3b'}$ are each independently halo or C$_1$-C$_6$ alkoxy.

In yet other embodiments, R$^{4a}$, R$^{4b}$ and R$^{4c}$ are each independently H. In other different embodiments, R$^{4a'}$, R$^{4b'}$ and R$^{4c'}$ are each independently H.

In various embodiments of the foregoing, X is halo, for example bromo.

In some embodiments, the compound of structure (II) has one of the following structures:

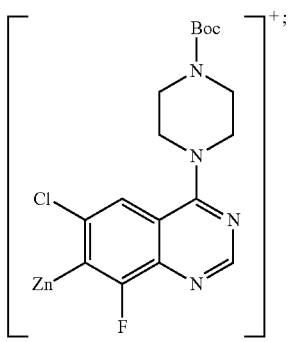
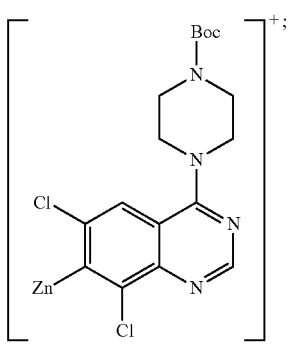
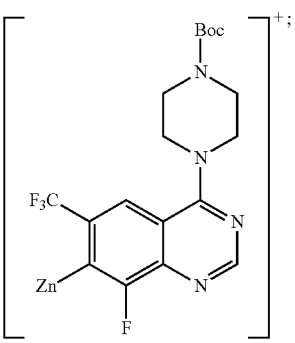
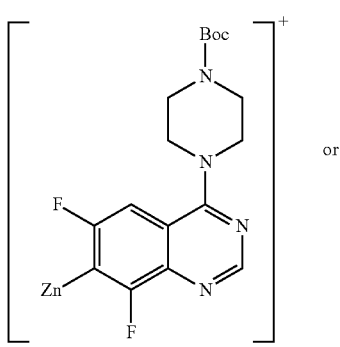
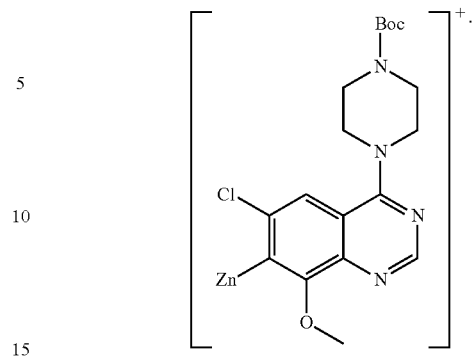
In yet other embodiments, the compound of structure (III) has one of the following structures:
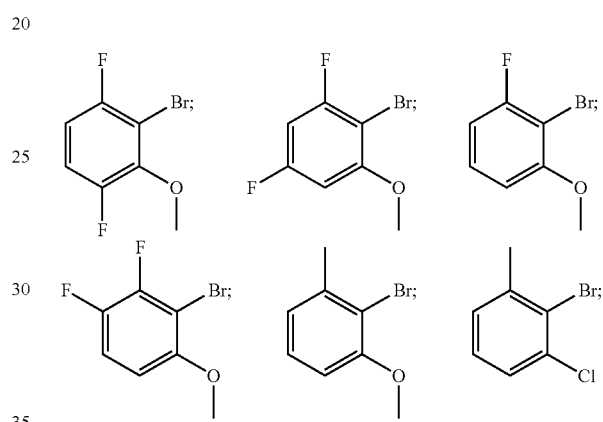
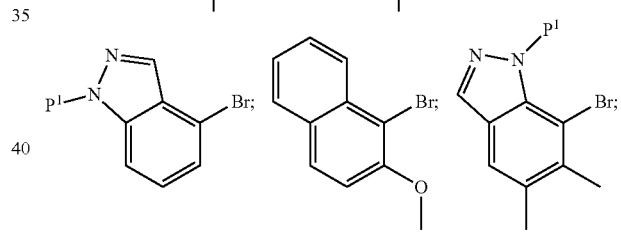
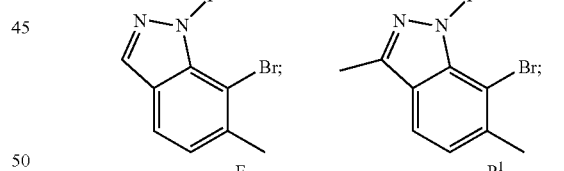
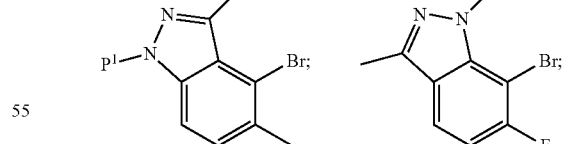
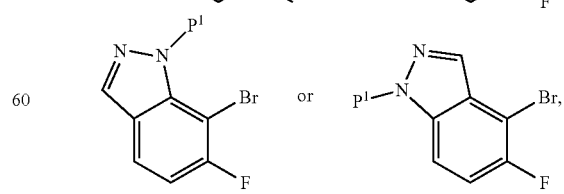
wherein $P^1$ is nitrogen protecting group, such as butyloxycarbonyl.

In some other more specific embodiments, the method comprises the following steps (a) and (b):

(a)

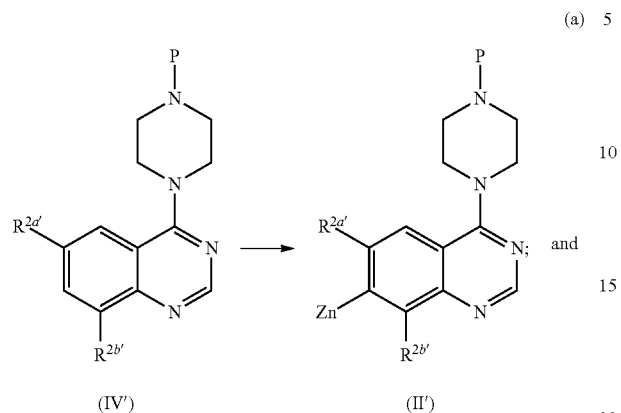

(IV')  (II')

(b)

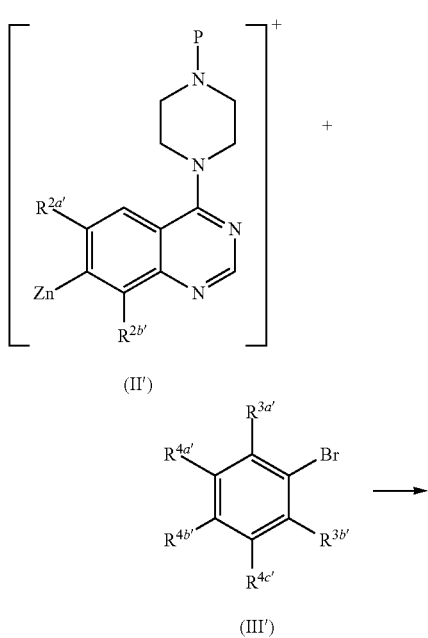

-continued

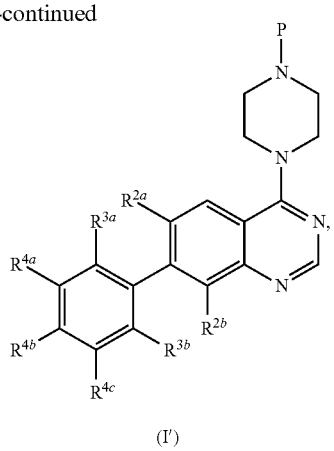

(I')

wherein:

$R^{2a}$, $R^{2b}$, $R^{2a'}$ and $R^{2b'}$ are each independently halo;

$R^{3a}$, $R^{3b}$, $R^{3a'}$ and $R^{3b'}$ are each independently halo, protected hydroxyl or $C_1$-$C_6$ alkoxy; and $R^{4a}$, $R^{4b}$, $R^{4c}$, $R^{4a'}$, $R^{4b'}$ and $R^{4c'}$ are each independently H.

In some embodiments, P is butyloxycarbonyl.

In some more embodiments, $R^{2a}$, $R^{2b}$, $R^{2a'}$ and $R^{2b'}$ are each independently chloro or fluoro. For example, in certain embodiments $R^{2a}$ and $R^{2b'}$ are each chloro, and $R^{2b}$ and $R^{2b'}$ are each fluoro.

In some other embodiments of the foregoing, $R^{3a}$, $R^{3b}$, $R^{3a'}$ and $R^{3b'}$ are each independently halo or $C_1$-$C_6$ alkoxy. In some of these embodiments halo is fluoro and $C_1$-$C_6$ alkoxy is methoxy. For example, in certain embodiments $R^{3a}$ and $R^{3a'}$ are each fluoro, and $R^{3b}$ and $R^{3b'}$ are each methoxy.

The methods disclosed herein can be used for preparation of various compounds of structure (I). In certain embodiments, the compound of structure (I) is selected from one of the compounds in Table 1.

TABLE 1

Representative Compounds of Structure I

| No. | Structure | Name |
|---|---|---|
| 1 | 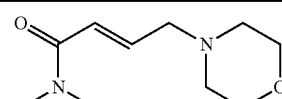 | (E)-1-(4-(6-chloro-8-fluoro-7-(2-fluoro-6-hydroxyphenyl)quinazolin-4-yl)piperazin-1-yl)-4-morpholinobut-2-en-1-one |

TABLE 1-continued

Representative Compounds of Structure I

| No. | Structure | Name |
|---|---|---|
| 2 | 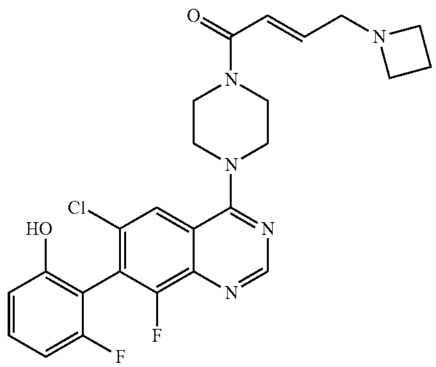 [SMILES: O=C(/C=C/CN1CCC1)N1CCN(c2ncnc3c(F)c(-c4c(O)cccc4F)c(Cl)cc23)CC1] | (E)-4-(azetidin-1-yl)-1-(4-(6-chloro-8-fluoro-7-(2-fluoro-6-hydroxyphenyl)quinazolin-4-yl)piperazin-1-yl)but-2-en-1-one |
| 3 | 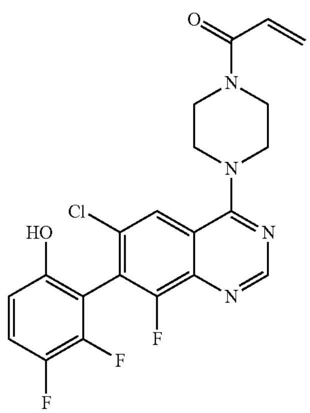 [SMILES: C=CC(=O)N1CCN(c2ncnc3c(F)c(-c4c(O)ccc(F)c4F)c(Cl)cc23)CC1] | 1-(4-(6-chloro-7-(2,3-difluoro-6-hydroxyphenyl)-8-fluoroquinazolin-4-yl)piperazin-1-yl)prop-2-en-1-one |
| 4 | 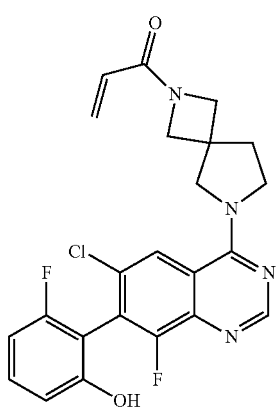 [SMILES: C=CC(=O)N1CC2(CCN(c3ncnc4c(F)c(-c5c(O)cccc5F)c(Cl)cc34)C2)C1] | 1-(6-(6-chloro-8-fluoro-7-(2-fluoro-6-hydroxyphenyl)quinazolin-4-yl)-2,6-diazaspiro[3.4]octan-2-yl)prop-2-en-1-one |
| 5 | 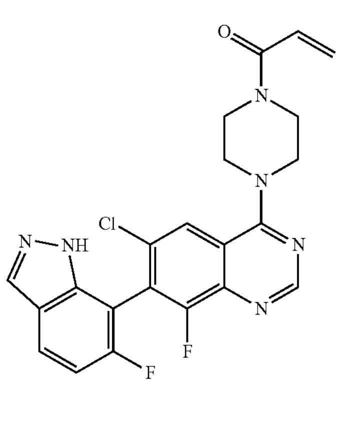 [SMILES: C=CC(=O)N1CCN(c2ncnc3c(F)c(-c4c(F)ccc5cn[nH]c45)c(Cl)cc23)CC1] | 1-(4-(6-chloro-8-fluoro-7-(6-fluoro-1H-indazol-7-yl)quinazolin-4-yl)piperazin-1-yl)prop-2-en-1-one |

TABLE 1-continued
Representative Compounds of Structure I
| No. | Structure | Name |
|---|---|---|
| 6 | 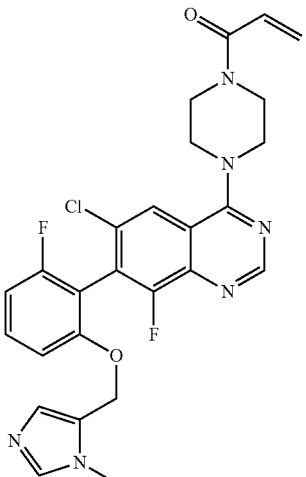 | 1-(4-(6-chloro-8-fluoro-7-(2-fluoro-6-((1-methyl-1H-imidazol-5-yl)methoxy)phenyl)quinazolin-4-yl)piperazin-1-yl)prop-2-en-1-one |
| 7 | 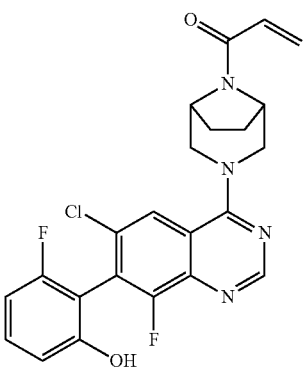 [SMILES: C=CC(=O)N1C2CCC1CN(c1ncnc3c(F)c(-c4c(O)cccc4F)c(Cl)cc13)C2] | 1-((1R,5S)-3-(6-chloro-8-fluoro-7-(2-fluoro-6-hydroxyphenyl)quinazolin-4-yl)-3,8-diazabicyclo[3.2.1]octan-8-yl)prop-2-en-1-one |
| 8 | 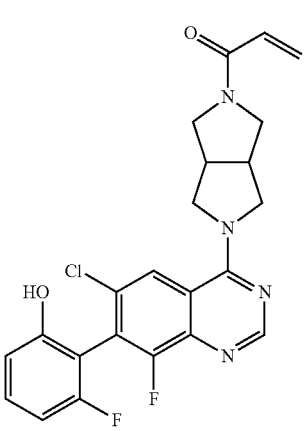 [SMILES: C=CC(=O)N1CC2CN(c3ncnc4c(F)c(-c5c(O)cccc5F)c(Cl)cc34)CC2C1] | 1-(5-(6-chloro-8-fluoro-7-(2-fluoro-6-hydroxyphenyl)quinazolin-4-yl)hexahydropyrrolo[3,4-c]pyrrol-2(1H)-yl)prop-2-en-1-one |

TABLE 1-continued

Representative Compounds of Structure I

| No. | Structure | Name |
|---|---|---|
| 9 | 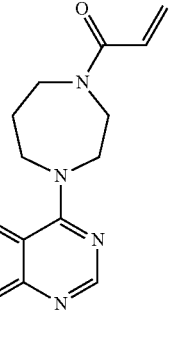 | 1-(4-(6-chloro-8-fluoro-7-(2-fluoro-6-hydroxyphenyl)quinazolin-4-yl)-1,4-diazepan-1-yl)prop-2-en-1-one |
| 10 | 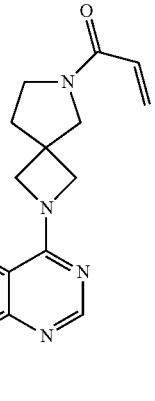 | 1-(2-(6-chloro-8-fluoro-7-(2-fluoro-6-hydroxyphenyl)quinazolin-4-yl)-2,6-diazaspiro[3.4]octan-6-yl)prop-2-en-1-one |
| 11 | 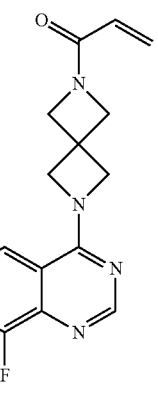 | 1-(6-(6-chloro-8-fluoro-7-(2-fluoro-6-hydroxyphenyl)quinazolin-4-yl)-2,6-diazaspiro[3.3]heptan-2-yl)prop-2-en-1-one |
| 12 | 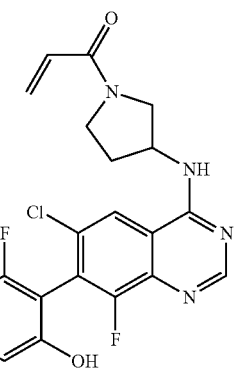 | 1-(3-((6-chloro-8-fluoro-7-(2-fluoro-6-hydroxyphenyl)quinazolin-4-yl)amino)pyrrolidin-1-yl)prop-2-en-1-one |

TABLE 1-continued
Representative Compounds of Structure I
| No. | Structure | Name |
|---|---|---|
| 13 | 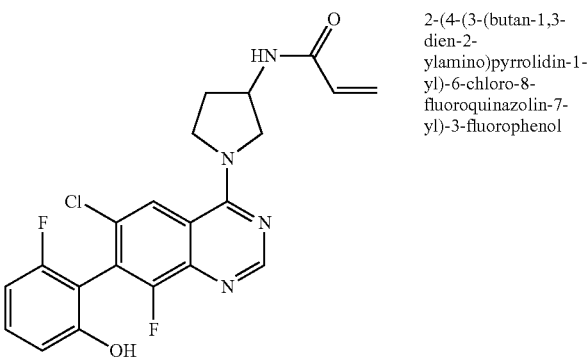 | 2-(4-(3-(butan-1,3-dien-2-ylamino)pyrrolidin-1-yl)-6-chloro-8-fluoroquinazolin-7-yl)-3-fluorophenol |
| 14 | 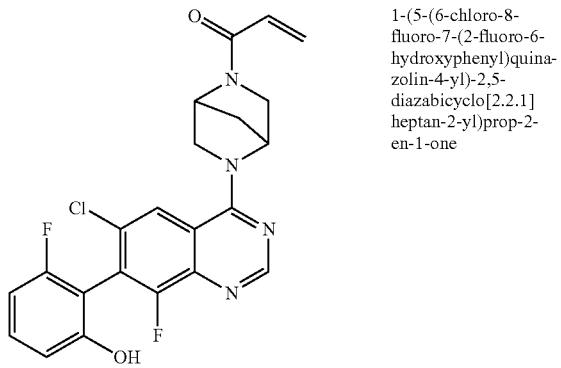 | 1-(5-(6-chloro-8-fluoro-7-(2-fluoro-6-hydroxyphenyl)quinazolin-4-yl)-2,5-diazabicyclo[2.2.1]heptan-2-yl)prop-2-en-1-one |
| 15 | 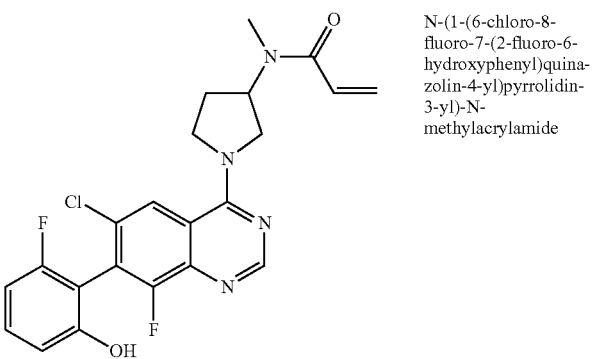 | N-(1-(6-chloro-8-fluoro-7-(2-fluoro-6-hydroxyphenyl)quinazolin-4-yl)pyrrolidin-3-yl)-N-methylacrylamide |

TABLE 1-continued

Representative Compounds of Structure I

| No. | Structure | Name |
|---|---|---|
| 16 | 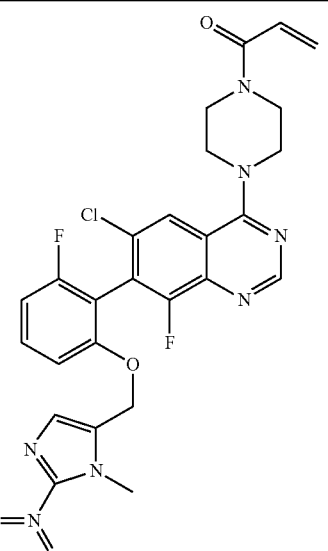 | 1-(4-(6-chloro-8-fluoro-7-(2-fluoro-6-((1-methyl-2-nitro-1H-imidazol-5-yl)methoxy)phenyl)quinazolin-4-yl)piperazin-1-yl)prop-2-en-1-one |
| 17 | 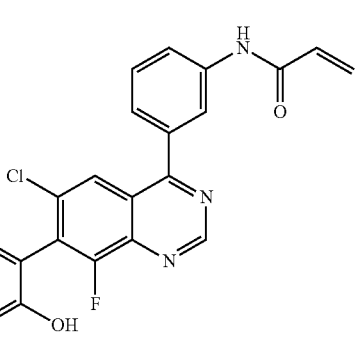 | N-(3-(6-chloro-8-fluoro-7-(2-fluoro-6-hydroxyphenyl)quinazolin-4-yl)phenyl)acrylamide |
| 18 | 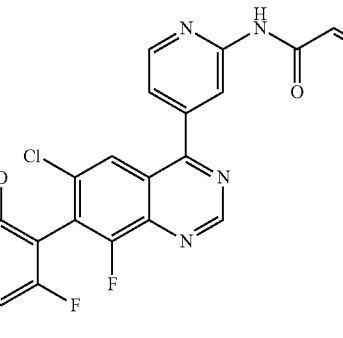 | N-(4-(6-chloro-8-fluoro-7-(2-fluoro-6-hydroxyphenyl)quinazolin-4-yl)pyridin-2-yl)acrylamide |
| 19 | 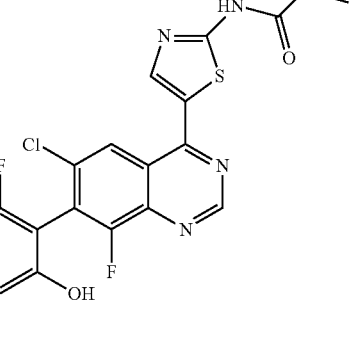 | N-(5-(6-chloro-8-fluoro-7-(2-fluoro-6-hydroxyphenyl)quinazolin-4-yl)thiazol-2-yl)acrylamide |

TABLE 1-continued

Representative Compounds of Structure I

| No. | Structure | Name |
|---|---|---|
| 20 | 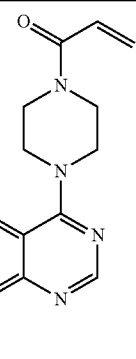 | 1-(4-(6-chloro-8-fluoro-7-(2-fluoro-6-hydroxyphenyl)quinazolin-4-yl)piperazin-1-yl)prop-2-en-1-one |
| 21 | 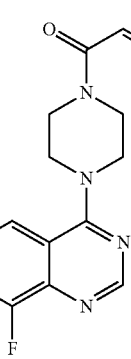 | 1-(4-(6-chloro-8-fluoro-7-(5-methyl-1H-indazol-4-yl)quinazolin-4-yl)piperazin-1-yl)prop-2-en-1-one |
| 22 | 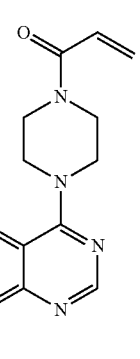 | 1-(4-(6-chloro-8-fluoro-7-(2-hydroxynaphthalen-1-yl)quinazolin-4-yl)piperazin-1-yl)prop-2-en-1-one |
| 23 | 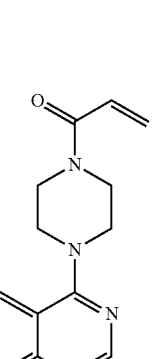 | (R)-1-(4-(6-chloro-8-fluoro-7-(2-fluoro-6-hydroxyphenyl)quinazolin-4-yl)piperazin-1-yl)prop-2-en-1-one |

TABLE 1-continued

Representative Compounds of Structure I

| No. | Structure | Name |
|---|---|---|
| 24 | 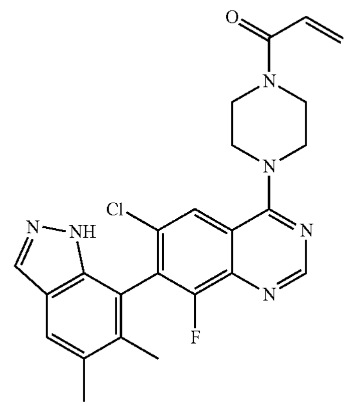 [SMILES: C=CC(=O)N1CCN(c2ncnc3c(F)c(-c4c(C)c(C)cc5cn[nH]c45)c(Cl)cc23)CC1] | 1-(4-(6-chloro-7-(5,6-dimethyl-1H-indazol-7-yl)-8-fluoroquinazolin-4-yl)piperazin-1-yl)prop-2-en-1-one |
| 25 | 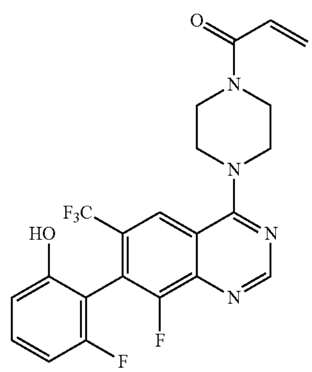 [SMILES: C=CC(=O)N1CCN(c2ncnc3c(F)c(-c4c(O)cccc4F)c(C(F)(F)F)cc23)CC1] | 1-(4-(8-fluoro-7-(2-fluoro-6-hydroxyphenyl)-6-(trifluoromethyl)quinazolin-4-yl)piperazin-1-yl)prop-1-en-1-one |
| 26 | 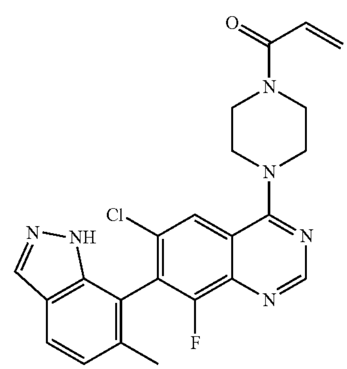 [SMILES: C=CC(=O)N1CCN(c2ncnc3c(F)c(-c4c(C)ccc5cn[nH]c45)c(Cl)cc23)CC1] | 1-(4-(6-chloro-8-fluoro-7-(6-methyl-1H-indazol-7-yl)quinazolin-4-yl)piperazin-1-yl)prop-2-en-1-one |
| 27 | 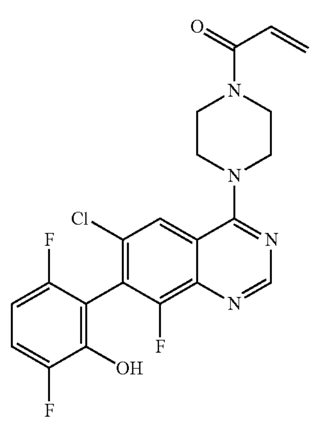 [SMILES: C=CC(=O)N1CCN(c2ncnc3c(F)c(-c4c(F)ccc(F)c4O)c(Cl)cc23)CC1] | 1-(4-(6-chloro-7-(3,6-difluoro-2-hydroxyphenyl)-8-fluoroquinazolin-4-yl)piperazin-1-yl)prop-2-en-1-one |

TABLE 1-continued
Representative Compounds of Structure I
| No. | Structure | Name |
|-----|-----------|------|
| 28 | 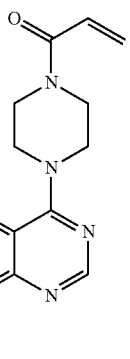 | 1-(4-(6-chloro-7-(2,4-difluoro-6-hydroxyphenyl)-8-fluoroquinazolin-4-yl)piperazin-1-yl)prop-2-en-1-one |
| 29 | 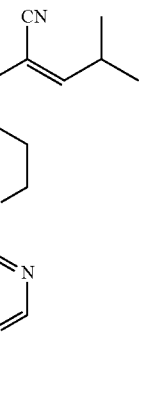 | (E)-2-(4-(6-chloro-8-fluoro-7-(2-fluoro-6-hydroxyphenyl)quinazolin-4-yl)piperazine-1-carbonyl)-4-methylpent-2-enenitrile |
| 30 | 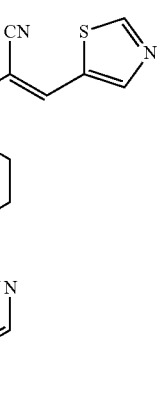 | (E)-2-(4-(6-chloro-8-fluoro-7-(2-fluoro-6-hydroxyphenyl)quinazolin-4-yl)piperazine-1-carbonyl)-3-(thiazol-5-yl)acrylonitrile |

TABLE 1-continued
Representative Compounds of Structure I
| No. | Structure | Name |
|---|---|---|
| 31 | 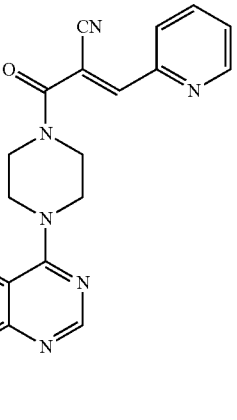 | (E)-2-(4-(6-chloro-8-fluoro-7-(2-fluoro-6-hydroxyphenyl)quinazolin-4-yl)piperazine-1-carbonyl)-3-(pyridin-2-yl)acrylonitrile |
| 32 | 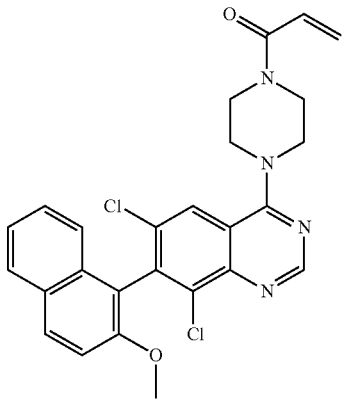 [SMILES: C=CC(=O)N1CCN(c2ncnc3c(Cl)c(-c4c(OC)ccc5ccccc45)c(Cl)cc23)CC1] | 1-(4-(6,8-dichloro-7-(2-methoxynaphthalen-1-yl)quinazolin-4-yl)piperazin-1-yl)prop-2-en-1-one |
| 33 | 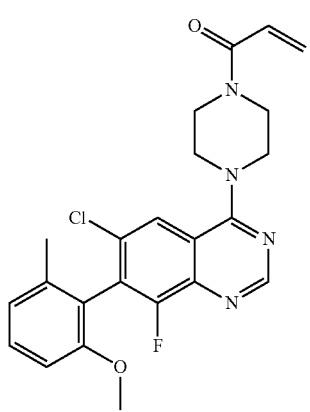 [SMILES: C=CC(=O)N1CCN(c2ncnc3c(F)c(-c4c(C)cccc4OC)c(Cl)cc23)CC1] | 1-(4-(6-chloro-8-fluoro-7-(2-methoxy-6-methylphenyl)quinazolin-4-yl)piperazin-1-yl)prop-2-en-1-one |

TABLE 1-continued

Representative Compounds of Structure I

| No. | Structure | Name |
|---|---|---|
| 34 | 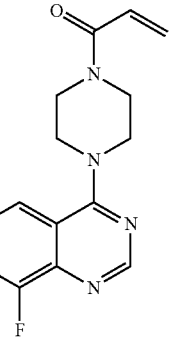 | 1-(4-(6-chloro-7-(2-chloro-6-methylphenyl)-8-fluoroquinazolin-4-yl)piperazin-1-yl)prop-2-en-1-one |
| 35 | 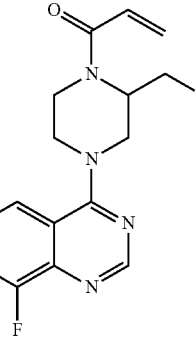 | 2-(1-acryloyl-4-(6-chloro-8-fluoro-7-(5-methyl-1H-indazol-4-yl)quinazolin-4-yl)piperazin-2-yl)acetonitrile |
| 36 | 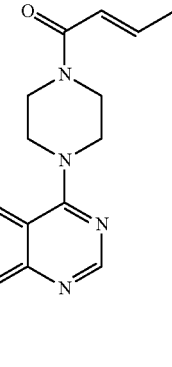 | (E)-1-(4-(6-chloro-8-fluoro-7-(5-methyl-1H-indazol-4-yl)quinazolin-4-yl)piperazin-1-yl)-4-(dimethylamino)but-2-en-1-one |
| 37 | 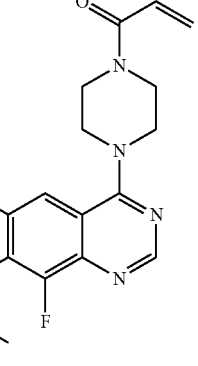 | 1-(4-(6,8-difluoro-7-(5-methyl-1H-indazol-4-yl)quinazolin-4-yl)piperazin-1-yl)prop-2-en-1-one |

TABLE 1-continued

Representative Compounds of Structure I

| No. | Structure | Name |
|---|---|---|
| 38 | 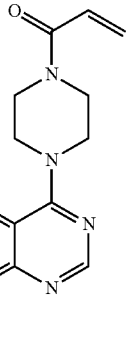 | 1-(4-(6,8-difluoro-7-(6-methyl-1H-indazol-7-yl)quinazolin-4-yl)piperazin-1-yl)prop-2-en-1-one |
| 39 | 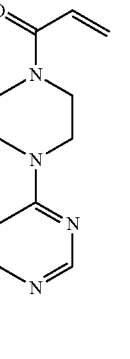 | 1-(4-(6,8-difluoro-7-(2-fluoro-6-hydroxyphenyl)quinazolin-4-yl)piperazin-1-yl)prop-2-en-1-one |
| 40 | 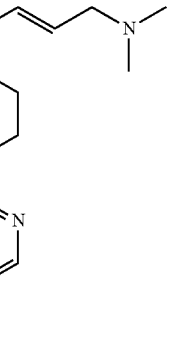 | (E)-1-(4-(6-chloro-8-fluoro-7-(2-fluoro-6-hydroxyphenyl)quinazolin-4-yl)piperazin-1-yl)-4-(dimethylamino)but-2-en-1-one |
| 41 | 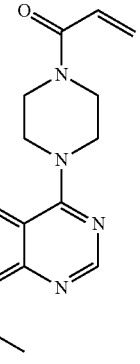 | 1-(4-(6-chloro-8-methoxy-7-(5-methyl-1H-indazol-4-yl)quinazolin-4-yl)piperazin-1-yl)prop-2-en-1-one |

TABLE 1-continued

Representative Compounds of Structure I

| No. | Structure | Name |
|---|---|---|
| 42 | 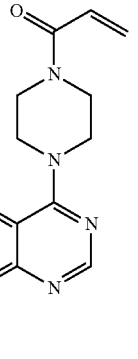 | 1-(4-(6,8-dichloro-7-(2-hydroxynaphthalen-1-yl)quinazolin-4-yl)piperazin-1-yl)prop-2-en-1-one |
| 43 | 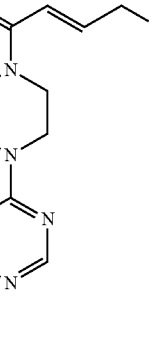 | (E)-4-amino-1-(4-(6-chloro-8-fluoro-7-(5-methyl-1H-indazol-4-yl)quinazolin-4-yl)piperazin-1-yl)but-2-en-1-one |
| 44 | 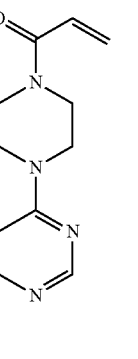 | 1-(4-(6-chloro-7-(2-fluoro-6-hydroxyphenyl)-8-methoxyquinazolin-4-yl)piperazin-1-yl)prop-2-en-1-one |
| 45 | 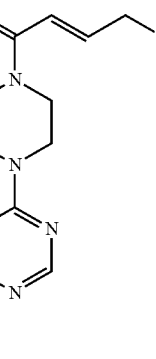 | (E)-1-(4-(6-chloro-8-fluoro-7-(5-methyl-1H-indazol-4-yl)quinazolin-4-yl)piperazin-1-yl)-4-hydroxybut-2-en-1-one |

TABLE 1-continued

Representative Compounds of Structure I

| No. | Structure | Name |
|---|---|---|
| 46 | 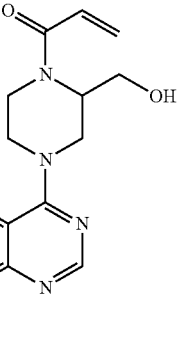 | 1-(4-(6-chloro-8-fluoro-7-(5-methyl-1H-indazol-4-yl)quinazolin-4-yl)-2-(hydroxymethyl)piperazin-1-yl)prop-2-en-1-one |
| 47 | 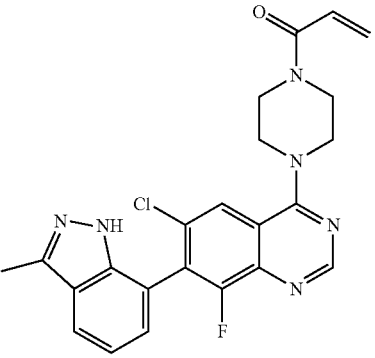 [SMILES: C=CC(=O)N1CCN(c2ncnc3c(F)c(-c4cccc5c(C)n[nH]c45)c(Cl)cc23)CC1] | 1-(4-(6-chloro-8-fluoro-7-(3-methyl-1H-indazol-7-yl)quinazolin-4-yl)piperazin-1-yl)prop-2-en-1-one |
| 48 | 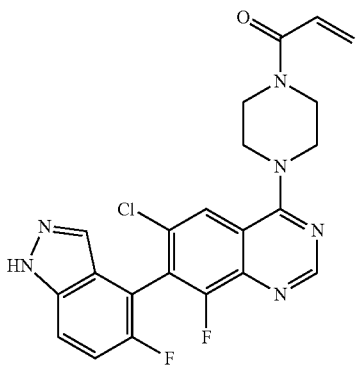 [SMILES: C=CC(=O)N1CCN(c2ncnc3c(F)c(-c4c(F)ccc5[nH]ncc45)c(Cl)cc23)CC1] | 1-(4-(6-chloro-8-fluoro-7-(5-fluoro-1H-indazol-4-yl)quinazolin-4-yl)piperazin-1-yl)prop-2-en-1-one |
| 49 | 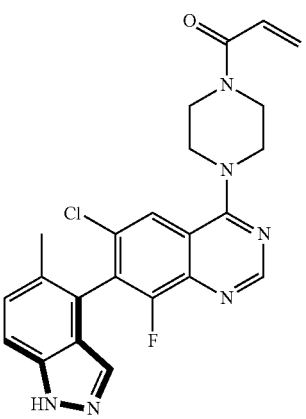 | (R)-1-(4-(6-chloro-8-fluoro-7-(5-methyl-1H-indazol-4-yl)quinazolin-4-yl)piperazin-1-yl)prop-2-en-1-one |

TABLE 1-continued

Representative Compounds of Structure I

| No. | Structure | Name |
|---|---|---|
| 50 | 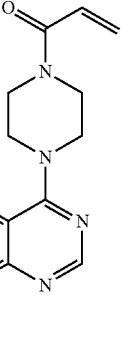 | 1-(4-(6-chloro-8-fluoro-7-(3-fluoro-5-methyl-1H-indazol-4-yl)quinazolin-4-yl)piperazin-1-yl)prop-2-en-1-one |
| 51 | 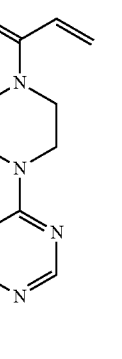 | (S)-1-(4-(6-chloro-8-fluoro-7-(2-fluoro-6-hydroxyphenyl)quinazolin-4-yl)piperazin-1-yl)prop-2-en-1-one |
| 52 | 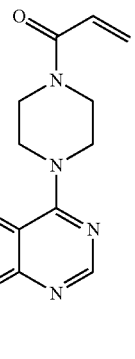 | 1-(4-(6-chloro-8-fluoro-7-(6-fluoro-3-methyl-1H-indazol-7-yl)quinazolin-4-yl)piperazin-1-yl)prop-2-en-1-one |
| 53 | 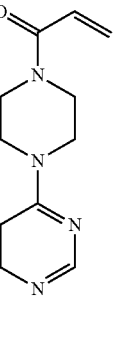 | 1-(4-(6-chloro-7-(2-((dimethylamino)methyl)-6-fluorophenyl)-8-fluoroquinazolin-4-yl)piperazin-1-yl)prop-2-en-1-one |

TABLE 1-continued

Representative Compounds of Structure I

| No. | Structure | Name |
| --- | --- | --- |
| 54 | 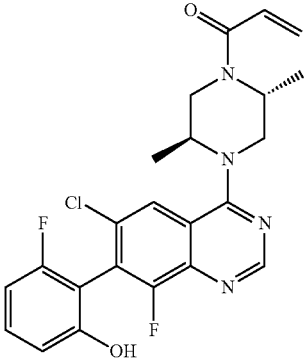 [SMILES: C=CC(=O)N1C[C@H](C)N(c2ncnc3c(F)c(-c4c(O)cccc4F)c(Cl)cc23)C[C@H]1C] | 1-((2R,5S)-4-(6-chloro-8-fluoro-7-(2-fluoro-6-hydroxyphenyl)quinazolin-4-yl)-2,5-dimethylpiperazin-1-yl)prop-2-en-1-one |
| 55 | 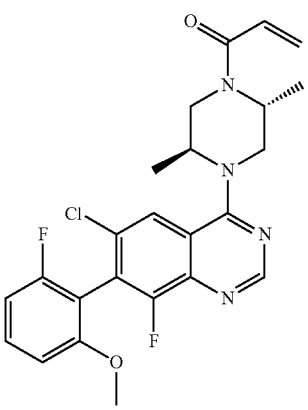 [SMILES: C=CC(=O)N1C[C@H](C)N(c2ncnc3c(F)c(-c4c(F)cccc4OC)c(Cl)cc23)C[C@H]1C] | 1-((2R,5S)-4-(6-chloro-8-fluoro-7-(2-fluoro-6-methoxyphenyl)quinazolin-4-yl)-2,5-dimethylpiperazin-1-yl)prop-2-en-1-one |
| 56 | 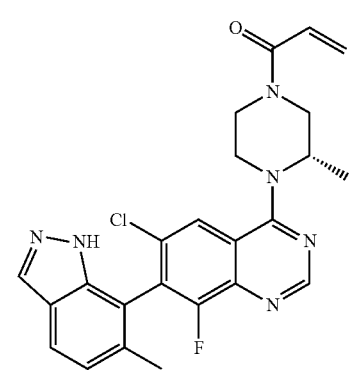 [SMILES: C=CC(=O)N1CCN(c2ncnc3c(F)c(-c4c(C)ccc5cn[nH]c45)c(Cl)cc23)[C@@H](C)C1] | 1-((3S)-4-(6-chloro-8-fluoro-7-(6-methyl-1H-indazol-7-yl)quinazolin-4-yl)-3-methylpiperazin-1-yl)prop-2-en-1-one |
| 57 | 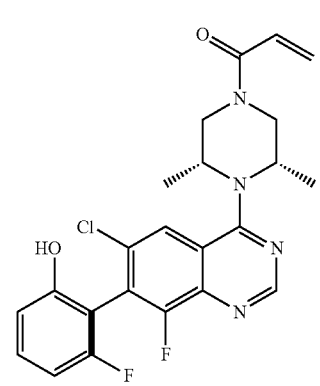 | 1-((3S,5R)-4-((R)-6-chloro-8-fluoro-7-(2-fluoro-6-hydroxyphenyl)quinazolin-4-yl)-3,5-dimethylpiperazin-1-yl)prop-2-en-1-one |

TABLE 1-continued

Representative Compounds of Structure I

| No. | Structure | Name |
|---|---|---|
| 58 | 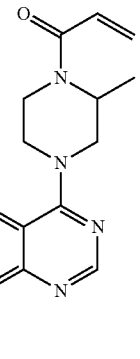 | 1-(4-(6-chloro-8-fluoro-7-(2-fluoro-6-hydroxyphenyl)quinazolin-4-yl)-2-methylpiperazin-1-yl)prop-2-en-1-one |
| 59 | 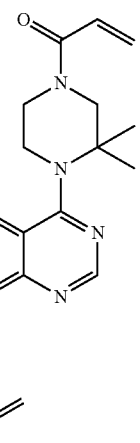 | 2-(4-(4-acryloyl-2,2-dimethylpiperazin-1-yl)-6-chloro-8-fluoroquinazolin-7-yl)-3-fluorophenyl acrylate |
| 60 | 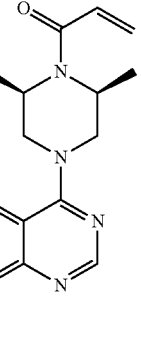 | 1-((2S,6R)-4-((S)-6-chloro-8-fluoro-7-(2-fluoro-6-hydroxyphenyl)quinazolin-4-yl)-2,6-dimethylpiperazin-1-yl)prop-2-en-1-one |
| 61 | 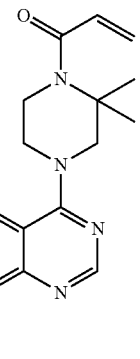 | 1-(4-(6-chloro-8-fluoro-7-(2-fluoro-6-hydroyxphenyl)quinazolin-4-yl)-2,2-dimethylpiperazin-1-yl)prop-2-en-1-one |

TABLE 1-continued

Representative Compounds of Structure I

| No. | Structure | Name |
|---|---|---|
| 62 | 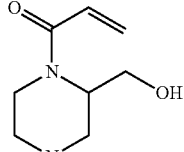 | 1-(4-(6-chloro-8-fluoro-7-(2-fluoro-6-hydroxyphenyl)quinazolin-4-yl)-2-(hydroxymethyl)piperazin-1-yl)prop-2-en-1-one |
| 63 | 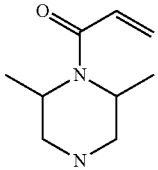 | 1-(4-(6-chloro-8-fluoro-7-(2-fluoro-6-hydroxyphenyl)quinazolin-4-yl)-2,6-dimethylpiperazin-1-yl)prop-2-en-1-one |
| 64 | 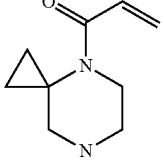 | 1-(7-(6-chloro-8-fluoro-7-(2-fluoro-6-hydroxyphenyl)quinazolin-4-yl)-4,7-diazaspiro[2.5]octan-4-yl)prop-2-en-1-one |
| 65 | 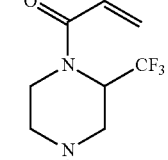 | 1-(4-(6-chloro-8-fluoro-7-(2-fluoro-6-hydroxyphenyl)quinazolin-4-yl)-2-(trifluoromethyl)piperazin-1-yl)prop-2-en-1-one |

TABLE 1-continued

Representative Compounds of Structure I

| No. | Structure | Name |
|-----|-----------|------|
| 66 | 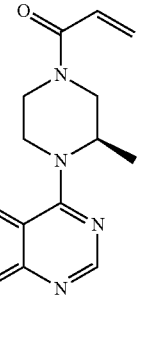 | 1-((3R)-4-(6-chloro-8-fluoro-7-(2-fluoro-6-hydroxphenyl)quinazolin-4-yl)-3-methylpiperazin-1-yl)prop-2-en-1-one |
| 67 | 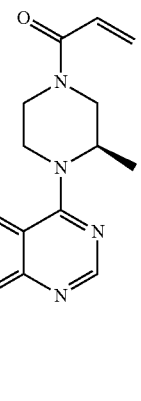 | 1-((3R)-4-(6-chloro-8-fluoro-7-(2-fluoro-6-methoxyphenyl)quinazolin-4-yl)-3-methylpiperazin-1-yl)prop-2-en-1-one |
| 68 | 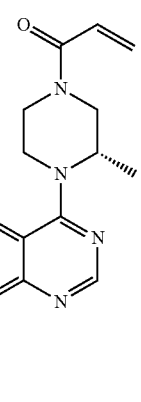 | 1-((3S)-4-(6-chloro-8-fluoro-7-(2-fluoro-6-hydroxyphenyl)quinazolin-4-yl)-3-methylpiperazin-1-yl)prop-2-en-1-one |
| 69 | 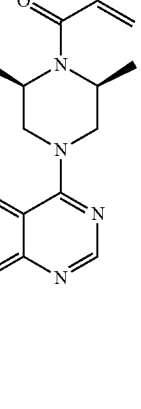 | 1-((2S,6R)-4-(6-chloro-8-fluoro-7-(2-fluoro-6-hydroxyphenyl)quinazolin-4-yl)-2,6-dimethylpiperazin-1-yl)prop-2-en-1-one |

TABLE 1-continued

Representative Compounds of Structure I

| No. | Structure | Name |
|---|---|---|
| 70 | 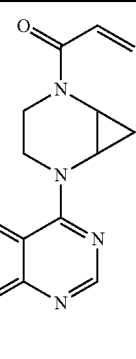 | 1-(5-(6-chloro-8-fluoro-7-(2-fluoro-6-hydroxyphenyl)quinazolin-4-yl)-2,5-diazabicyclo[4.1.0]heptan-2-yl)prop-2-en-1-one |
| 71 | 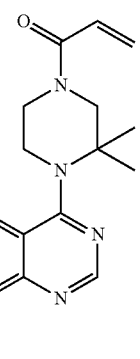 | 1-(4-(6-chloro-8-fluoro-7-(2-fluoro-6-hydroxyphenyl)quinazolin-4-yl)-3,3-dimethylpiperazin-1-yl)prop-2-en-1-one |
| 72 | 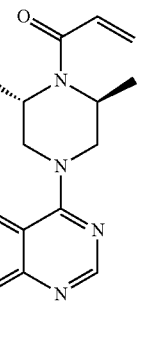 | 1-((2S,6S)-4-(6-chloro-8-fluoro-7-(2-fluoro-6-hydroxyphenyl)quinazolin-4-yl)-2,6-dimethylpiperazin-1-yl)prop-2-en-1-one |
| 73 | 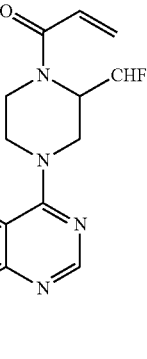 | 1-(4-(6-chloro-8-fluoro-7-(2-fluoro-6-hydroxyphenyl)quinazolin-4-yl)-2-(difluoromethyl)piperazin-1-yl)prop-2-en-1-one |

TABLE 1-continued

Representative Compounds of Structure I

| No. | Structure | Name |
|-----|-----------|------|
| 74 | 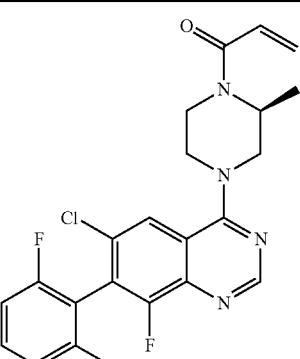 | 1-((2S)-4-(6-chloro-8-fluoro-7-(2-fluoro-6-hydroxyphenyl)quinazolin-4-yl)-2-methylpiperazin-1-yl)prop-2-en-1-one |
| 75 | 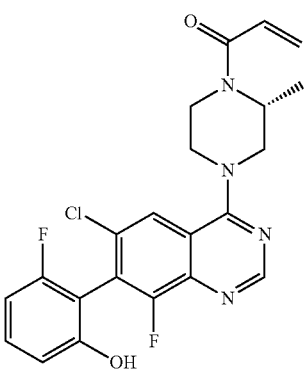 [SMILES: C=CC(=O)N1CCN(c2ncnc3c(F)c(-c4c(O)cccc4F)c(Cl)cc23)C[C@H]1C] | 1-((2R)-4-(6-chloro-8-fluoro-7-(2-fluoro-6-hydroxyphenyl)quinazolin-4-yl)-2-methylpiperazin-1-yl)prop-2-en-1-one |
| 76 | 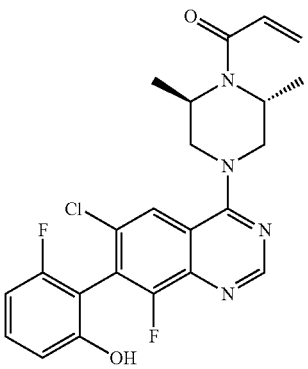 [SMILES: C=CC(=O)N1[C@H](C)CN(c2ncnc3c(F)c(-c4c(O)cccc4F)c(Cl)cc23)C[C@H]1C] | 1-((2R,6R)-4-(6-chloro-8-fluoro-7-(2-fluoro-6-hydroxyphenyl)quinazolin-4-yl)-2,6-dimethylpiperazin-1-yl)prop-2-en-1-one |
| 77 | 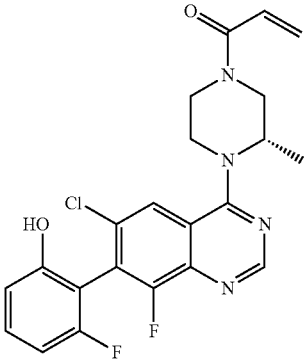 [SMILES: C=CC(=O)N1CCN(c2ncnc3c(F)c(-c4c(O)cccc4F)c(Cl)cc23)[C@@H](C)C1] | 1-((3S)-4-(6-chloro-8-fluoro-7-(2-fluoro-6-hydroxyphenyl)quinazolin-4-yl)-3-methylpiperazin-1-yl)prop-2-en-1-one |

TABLE 1-continued

Representative Compounds of Structure I

| No. | Structure | Name |
|---|---|---|
| 78 | 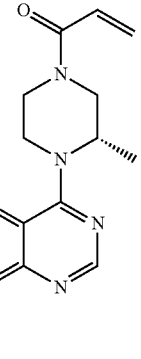 | 1-((S)-4-((S)-6-chloro-8-fluoro-7-(2-fluoro-6-hydroxyphenyl)quinazolin-4-yl)-3-methylpiperazin-1-yl)prop-2-en-1-one |
| 79 | 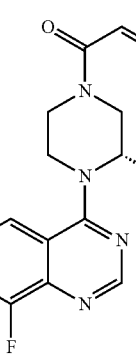 | 1-((3S)-4-(6-chloro-8-fluoro-7-(5-methyl-1H-indazol-4-yl)quinazolin-4-yl)-3-methylpiperazin-1-yl)prop-2-en-1-one |
| 80 | 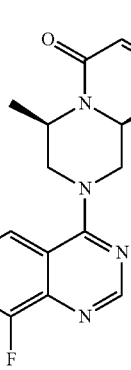 | 1-((2S,6R)-4-(6-chloro-8-fluoro-7-(5-methyl-1H-indazol-4-yl)quinazolin-4-yl)-2,6-dimethylpiperazin-1-yl)prop-2-en-1-one |
| 81 | 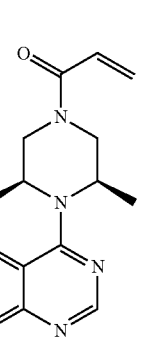 | 1-((3R,5S)-4-(6-chloro-8-fluoro-7-(2-fluoro-6-hydroxyphenyl)quinazolin-4-yl)-3,5-dimethylpiperazin-1-yl)prop-2-en-1-one |

TABLE 1-continued

Representative Compounds of Structure I

| No. | Structure | Name |
|---|---|---|
| 82 | 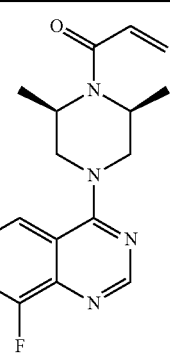 | 1-((2S,6R)-4-((R)-6-chloro-8-fluoro-7-(2-fluoro-6-hydroxyphenyl)quinazolin-4-yl)-2,6-dimethylpiperazin-1-yl)prop-2-en-1-one |
| 83 | 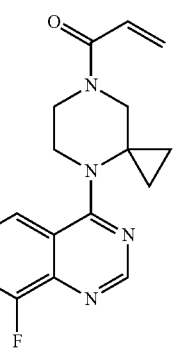 | 1-(4-(6-chloro-8-fluoro-7-(2-fluoro-6-hydroxyphenyl)quinazolin-4-yl)-4,7-diazaspiro[2.5]octan-7-yl)prop-2-en-1-one |
| 84 | 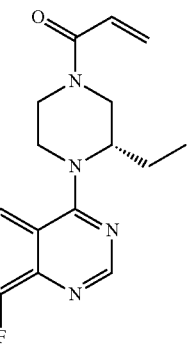 | 1-((3S)-4-(6-chloro-8-fluoro-7-(2-fluoro-6-hydroxyphenyl)quinazolin-4-yl)-3-ethylpiperazin-1-yl)prop-2-en-1-one |
| 85 | 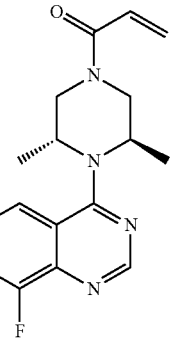 | 1-((3R,5R)-4-(6-chloro-8-fluoro-7-(2-fluoro-6-hydroxyphenyl)quinazolin-4-yl)-3,5-dimethylpiperazin-1-yl)prop-2-en-1-one |

TABLE 1-continued

Representative Compounds of Structure I

| No. | Structure | Name |
|---|---|---|
| 86 | 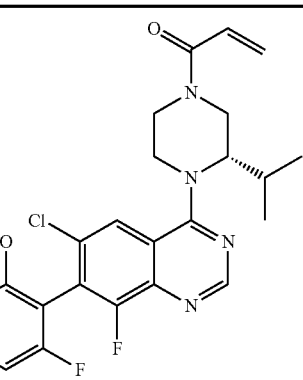 | 1-((3S)-4-(6-chloro-8-fluoro-7-(2-fluoro-6-hydroxyphenyl)quinazolin-4-yl)-3-isopropylpiperazin-1-yl)prop-2-en-1-one |
| 87 | 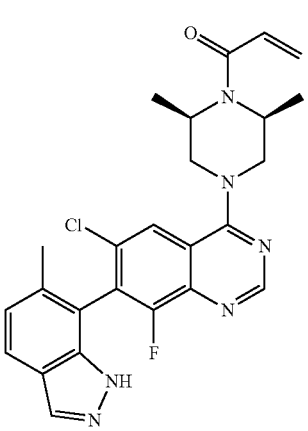 [SMILES: C=CC(=O)N1[C@H](C)CN(c2ncnc3c(F)c(-c4c(C)ccc5cn[nH]c45)c(Cl)cc23)C[C@@H]1C] | 1-((2S,6R)-4-(6-chloro-8-fluoro-7-(6-methyl-1H-indazol-7-yl)quinazolin-4-yl)-2,6-dimethylpiperazin-1-yl)prop-2-en-1-one |
| 88 | 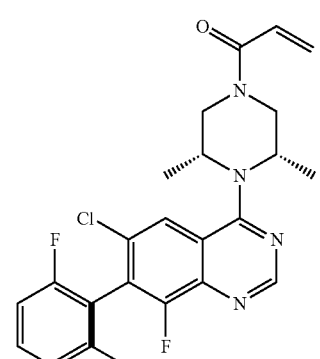 | 1-((3S,5R)-4-((S)-6-chloro-8-fluoro-7-(2-fluoro-6-hydroxyphenyl)quinazolin-4-yl)-3,5-dimethylpiperazin-1-yl)prop-2-en-1-one |
| 89 | 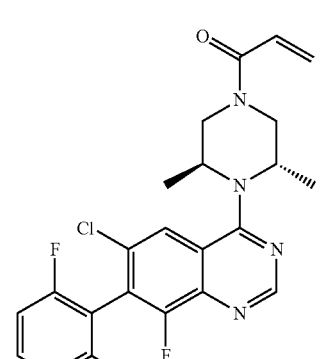 | 1-((3S,5S)-4-(6-chloro-8-fluoro-7-(2-fluoro-6-hydroxyphenyl)quinazolin-4-yl)-3,5-dimethylpiperazin-1-yl)prop-2-en-1-one |

TABLE 1-continued

Representative Compounds of Structure I

| No. | Structure | Name |
|---|---|---|
| 90 | 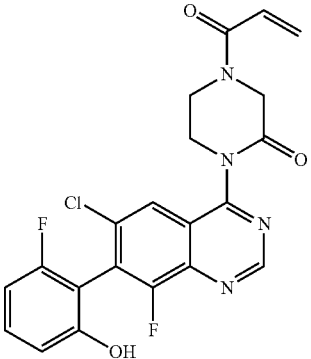 [SMILES: C=CC(=O)N1CCN(c2ncnc3c(F)c(-c4c(O)cccc4F)c(Cl)cc23)C(=O)C1] | 4-acryloyl-1-(6-chloro-8-fluoro-7-(2-fluoro-6-hydroxyphenyl)quinazolin-4-yl)piperazin-2-one |
| 91 | 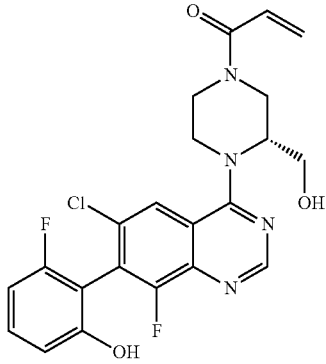 [SMILES: C=CC(=O)N1CCN(c2ncnc3c(F)c(-c4c(O)cccc4F)c(Cl)cc23)[C@@H](CO)C1] | 1-((3R)-4-(6-chloro-8-fluoro-7-(2-fluoro-6-hydroxyphenyl)quinazolin-4-yl)-3-(hydroxymethyl)piperazin-1-yl)prop-2-en-1-one |
| 92 | 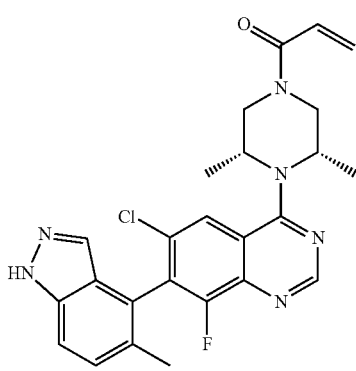 [SMILES: C=CC(=O)N1C[C@@H](C)N(c2ncnc3c(F)c(-c4c(C)ccc5[nH]ncc45)c(Cl)cc23)[C@@H](C)C1] | 1-((3S,5R)-4-(6-chloro-8-fluoro-7-(5-methyl-1H-indazol-4-yl)quinazolin-4-yl)-3,5-dimethylpiperazin-1-yl)prop-2-en-1-one |
| 93 | 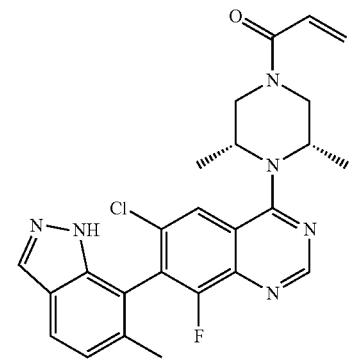 [SMILES: C=CC(=O)N1C[C@@H](C)N(c2ncnc3c(F)c(-c4c(C)ccc5cn[nH]c45)c(Cl)cc23)[C@@H](C)C1] | 1-((3S,5R)-4-(6-chloro-8-fluoro-7-(6-methyl-1H-indazol-7-yl)quinazolin-4-yl)-3,5-dimethylpiperazin-1-yl)prop-2-en-1-one |

The present disclosure also provides various compounds useful in embodiments of the methods. For example, in one embodiment is provided a compound having the following structure (II):

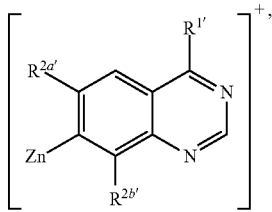

(II)

wherein:

$R^{1'}$ is a non-hydrogen, non-acidic substituent; and $R^{2a'}$ and $R^{2b'}$ are each independently halo, protected hydroxyl, $C_1$-$C_6$ alkyl, $C_1$-$C_6$ haloalkyl or $C_1$-$C_6$ alkoxy.

In some embodiments of the foregoing compounds, $R^{1'}$ is $C_1$-$C_6$ alkyl, carbocyclyl or heterocyclyl. For example, in some embodiments $R^{1'}$ is heterocyclyl, such as piperazinyl. In more specific embodiments $R^{1'}$ has the following structure:

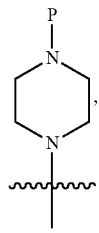

wherein P is a nitrogen protecting group, such as butyloxycarbonyl (Boc).

In other different embodiments, $R^{2a'}$ and $R^{2b'}$ are each independently halo. For example, in certain embodiments $R^{2a'}$ and $R^{2b'}$ are independently chloro or fluoro. In some more specific embodiments, $R^{2a'}$ is chloro and $R^{2b'}$ is fluoro.

In certain embodiments, the compound has the following structure:

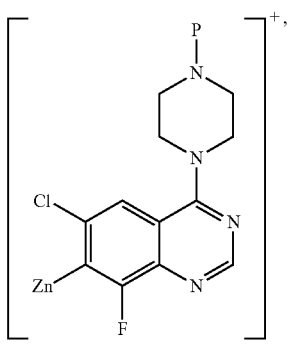

wherein P is a nitrogen protecting group, such as butyloxycarbonyl.

In some other embodiments, the disclosure provides a compound having the following structure (V):

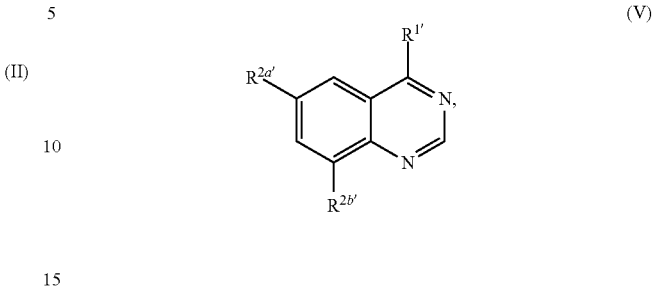

(V)

or a salt thereof, wherein:

$R^{1'}$ is heterocyclyl; and $R^{2a'}$ and $R^{2b'}$ are each independently halo, protected hydroxyl, $C_1$-$C_6$ alkyl, $C_1$-$C_6$ haloalkyl or $C_1$-$C_6$ alkoxy.

In certain embodiments of compound (V), heterocyclyl is piperazinyl. For example, in some embodiments $R^{1'}$ has the following structure:

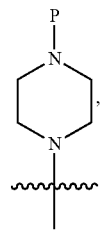

wherein P is a nitrogen protecting group, such as butyloxycarbonyl (Boc).

In other embodiments, $R^{2a'}$ and $R^{2b'}$ are each independently halo. In some of these embodiments, $R^{2a'}$ and $R^{2b'}$ are independently chloro or fluoro. For example, in certain embodiments $R^{2a'}$ is chloro and $R^{2b'}$ is fluoro.

In some more specific embodiments, the compound has the following structure:

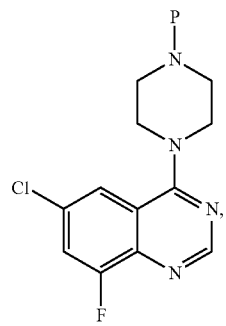

wherein P is a nitrogen protecting group, such as butyloxycarbonyl.

EXAMPLES

Example 1

Preparation of Compound 2

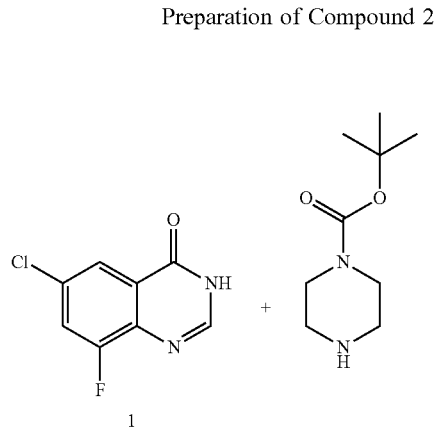

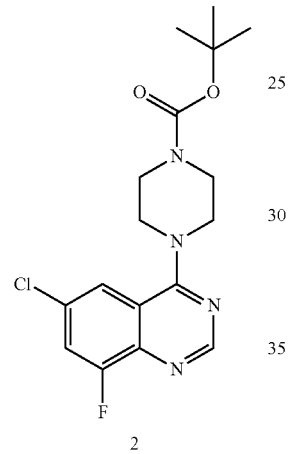

In a 4-neck, 3 L, round-bottom flask with a magnetic stir bar, compound 1 (82.47 g, 0.4153 mol, 1 equiv), BOP (201 g, 0.4544 mol, 1.1 equiv), and DBU (78.8 mL, 0.5272 mol, 1.3 equiv) were slurried in THF (2.1 L). After 30 minutes, N-Boc-piperazine (100 g, 0.5368 mol, 1.3 equiv) was added. The reaction mixture was stirred at 70° C. overnight to form a dark solution. The reaction was concentrated to one half volume via rotary evaporator, quenched with water (600 mL), then extracted with EtOAc (3×400 mL). The combined organic layers were dried ($Na_2SO_4$) and concentrated to an oil. The dark oil was stirred in 1:1 EtOAc/$Et_2O$ (700 mL) overnight to form solids. The solids were filtered to recover 90 g of crude 2. The impure product was slurried overnight in warm EtOAc (700 mL) then filtered to recover 10 g of starting material 1. The filtrate was then concentrated and slurried in 3:1 EtOAc/$Et_2O$ (300/100 mL) overnight. The solids were filtered and washed with 4:1 hexane/$Et_2O$ to recover 60 g of compound 2. All remaining impure product was combined and purified via a short plug column of silica gel with 1:4 EtOAc/hexane as eluent. All fractions containing product were combined and slurried in minimum 4:1 EtOAc/hexane (300 mL) overnight. The solids were filtered to recover another 43 g of 2 for a total combined amount of 103 g (67%). $^1$H NMR (500 MHz, $CDCl_3$) δ 8.77 (s, 1H), 7.64 (t, J=1.8 Hz, 1H), 7.46 (dd, J=9.4, 2.2 Hz, 1H), 3.79-3.74 (m, 4H), 3.67-3.63 (m, 4H), 1.50 (s, 9H).

Example 2

Preparation of Compound 4

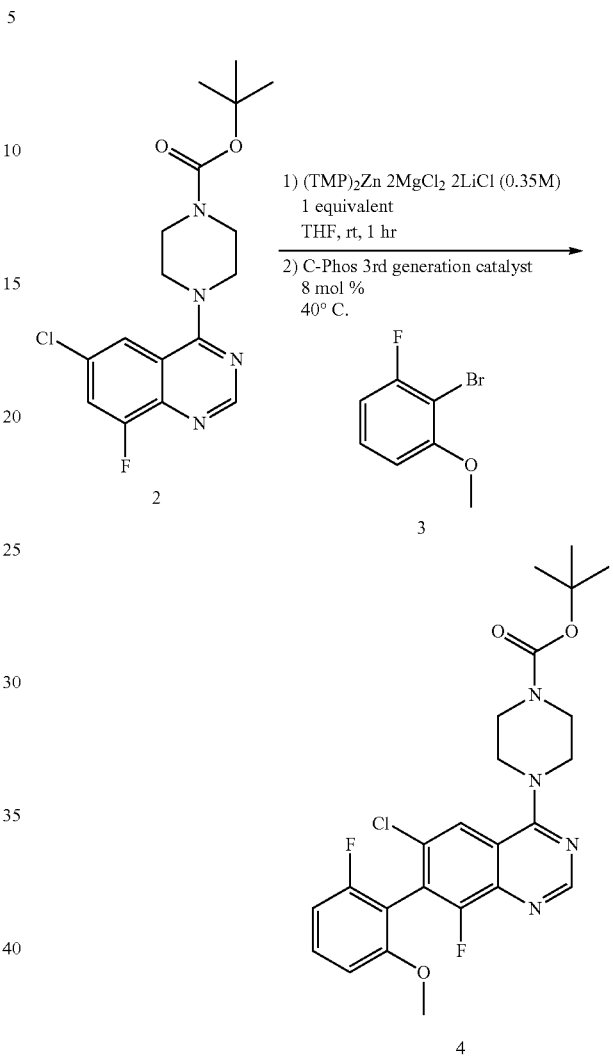

A dried 3 L, 3-neck flask (evacuated under vacuum and filled with $N_2$ three times) was fitted with mechanical stirring, temperature probe, and nitrogen inlet and charged with tert-butyl 4-(6-chloro-8-fluoroquinazolin-4-yl)piperazine-1-carboxylate 2 (100 g, 272.6 mmol) and dry THF (1 L). Bis(2,2,6,6-tetramethylpiperidinyl)zinc, lithium chloride, magnesium chloride complex (($TMP)_2$ $Zn.2MgCl_2.2LiCl$) (778.9 mL of a 0.35 M solution in THF/toluene, 272.6 mmol) was added via addition funnel over 10 minutes. The reaction was allowed to stir for 45 min at room temperature then degassed by bubbling nitrogen through the solution for 15 minutes. Solid 2-bromo-1-fluoro-3-methoxybenzene (55.9 g, 272.6 mmol) and CPhos $3^{rd}$ generation precatalyst (17.6 g, 21.8 mmol) were added, and the mixture was heated to 40° C. for 12 h. The reaction was cooled in an ice bath and slowly quenched with 1.5 L of a 1:1 solution of saturated ammonium chloride and $H_2O$. The layers were separated, and the aqueous layer was extracted with DCM (800 mL). The combined organic layers were dried ($MgSO_4$), and the solvent was removed under vacuum. The residue was slurried in isopropyl alcohol (IPA, 1 L) at room temperature for 10 min then at 60° C. for 1 hour. Upon cooling to room temperature overnight, the solid was collected by vacuum filtration and washed with IPA (2×250 mL) yielding a pale yellow solid (64.83 g, 48.4% yield). The remaining material in the filtrate was adsorbed onto 250 g silica gel and purified by flash column chromatography (750 g silica gel column (dry loaded), stepwise gradient of 20%-40% EtOAc in hexanes). The pure fractions were concentrated, and the resulting solid was triturated with IPA (300 mL) at 60° C. for 1 hour. Upon cooling to room temperature overnight, the solid was collected by vacuum filtration and washed with IPA (2×100 mL) yielding a pale yellow solid (30.2 g, 22.5% yield). Total yield=95.03 g (71%). $^1$H NMR (400 MHz, CDCl$_3$) δ 8.80 (s, 1H), 7.84-7.76 (d, J=1.5 Hz, 1H), 7.50-7.39 (m, 1H), 6.91-6.80 (m, 2H), 3.92-3.75 (m, 7H), 3.73-3.62 (m, 4H), 1.51 (s, 9H).

Example 3

Preparation of Compound 5

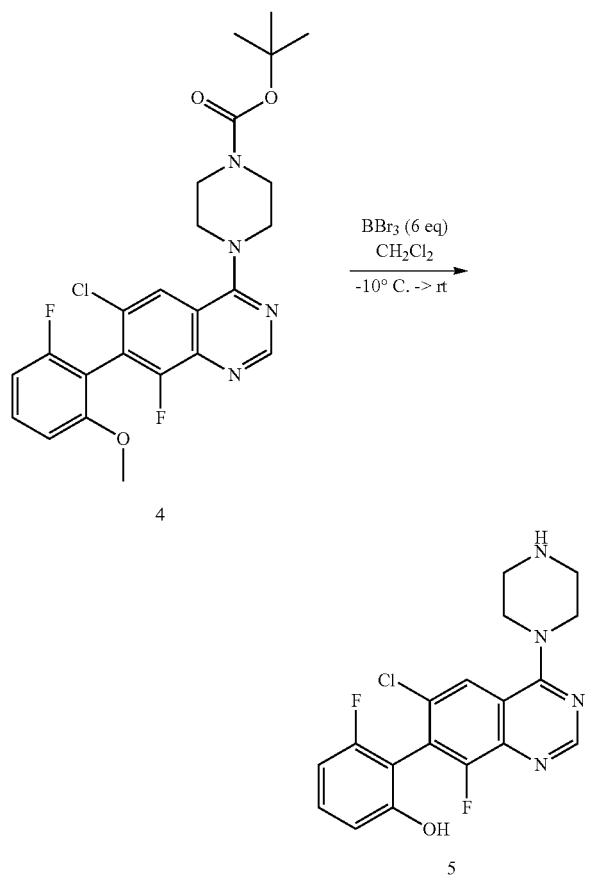

A 5 L, multi-neck, jacketed reactor with bottom valve was purged with N$_2$ and charged with tert-butyl 4-(6-chloro-8-fluoro-7-(2-fluoro-6-methoxyphenyl)quinazolin-4-yl)piperazine-1-carboxylate 6 and CH$_2$Cl$_2$ (1260 mL). The mixture was cooled to −10° C. Neat BBr$_3$ (106 mL, 1.1 mol, 6 equiv) was added in a slow stream via syringe over 11 min causing immediate precipitation of a tan solid and an exotherm to 3° C. After addition was complete, the reaction was warmed to room temperature, and the suspension was stirred for 19 h. HPLC analysis indicated good conversion to the desired piperazine intermediate 5 with just a small amount of methyl ether remaining. The reaction was cooled to −10° C. and very carefully quenched with an ice/water mixture (1 kg).

Example 4

Preparation of Compound 6

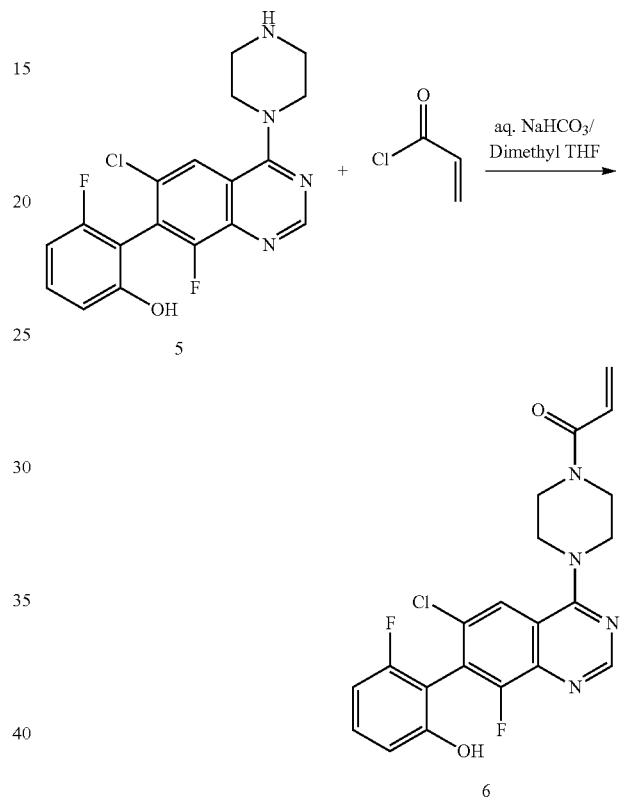

The ice and water was added very slowly at first allowing for quench to occur between additions. A maximum exothermic warming to 27° C. during the quench was observed. Additional water (1 L) was added, and the mixture was stirred 1.5 h to allow compound 5 to dissolve in the aqueous layer. The CH$_2$Cl$_2$ layer was drawn off through the reactor valve. CH$_2$Cl$_2$ (360 mL) was added; the layers were stirred for 30 min; and the CH$_2$Cl$_2$ layer was drawn off. The acidic aqueous phase was cooled to 10° C. and neutralized to pH 8 with 10 M NaOH added portion-wise, which caused precipitation of the free piperazine. Mild exothermic reaction warmed the vessel to 18° C. The piperazine solid aggregated into a gummy material which stuck to the bottom and sides of the reactor. 2-MeTHF (1440 mL) was added, and the mixture was stirred rapidly at room temp for several minutes to dissolve most of the solid. Solid NaHCO$_3$ (77 g, 0.92 mol, 5 eq.) was added, and the reaction was allowed to stir 30 min. With stirring maintained at a rate that gave thorough mixing of the layers, the acryloyl chloride (30 mL, 0.37 mol, 2 eq.) was added at 18° C. rapidly via syringe. No exothermic reaction was observed. The acylation was allowed to proceed for 2 h. The stirring was stopped, and the layers were allowed to separate. HPLC of the organic and aqueous layers showed complete consumption of the piperazine compound 5 and good conversion to the desired product 6. The layers were separated via the reactor valve. The aqueous layer was returned to the reactor and allowed to stir for 1 h with fresh 2-MeTHF (360 mL). Layers were again separated. The combined organic layers were dried (Na$_2$SO$_4$) and concentrated to give the crude product as a yellow-orange viscous oil that solidified upon standing overnight. Attempts to purify the product by trituration in various hot solvents were not successful. The product was purified by flash chromatography. Due to insolubility, it was necessary to dissolve the product in warm THF/DMF mixtures for loading onto the columns. The crude product was divided into 3 batches for initial columns (1.5 kg silica gel, elution with 1:1 EtOAc/hex, then 1:1 EtOAc/hex with 5% EtOH, then 1:1 EtOAc/hex with 10% EtOH). All mixed fractions were combined and re-chromatographed under the same conditions. Mixed fractions from the second round were again combined and re-chromatographed one final time. All pure fractions were combined and concentrated in vacuo to a wet, pasty solid. The material was then slurried in 5% EtOH/EtOAc at room temperature, collected by vacuum filtration, and washed with EtOAc. The product was dried in a vacuum oven overnight (house vacuum, ~10 tor, 50° C.) to provide 60.3 g (76%) of compound 6 as a colorless, light, flaky solid. $^1$H NMR (400 MHz, DMSO-d$_6$) δ 10.29 (s, 1H), 8.70 (s, 1H), 8.04 (s, 1H), 7.43-7.32 (m, 1H), 6.90-6.78 (m, 3H), 6.18 (dd, J=16.6, 2.2 Hz, 1H), 5.74 (dd, J=10.4, 2.2 Hz, 1H), 3.93 (broad s, 4H), 3.88-3.70 (m, 4H).

Example 5

Preparation of Compound 7

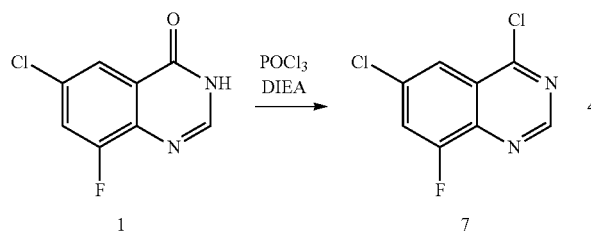

In a 1 L round-bottom flask with a magnetic stir bar, compound 1 (70 g, 0.3525 mol, 1.0 eq.) was slurried in POCl$_3$ (350 mL, 3.7663 mol, 10.7 eq.). Cautiously, DIEA (30 mL, 0.1741 mol, 0.5 eq.) was added to the mixture. The reaction mixture was heated to reflux overnight to form dark solution. HPLC analysis indicated complete reaction. The flask was fitted with a distillation head, and approximately one half the volume of POCl$_3$ (175 mL) was distilled off. While cooling to room temperature, product precipitated from the mixture. The solids were slurried in CH$_3$CN (1.2 L), and the slurry was slowly added to a vigorously stirred ice/water mixture (600 mL) while maintaining the internal temperature below 10° C. After 2 hours of stirring at 10° C. to hydrolyze the POCl$_3$, HPLC analysis showed the product also began to slowly hydrolyze to starting material 1. At this point, the precipitate was collected by vacuum filtration, washed with cold water, and dried overnight (house vacuum, ~10 torr, room temperature) to recover 46 grams (60%) of product 7. As the filtrate warmed to room temperature, a mild exothermic reaction was observed. HPLC analysis indicated the filtrate contained only 1. Compound 7 could be further isolated from the filtrate. The isolated 7 contained ca. 5% 1 and was used in the next step without further purification.

Example 6

Preparation of Compound 8

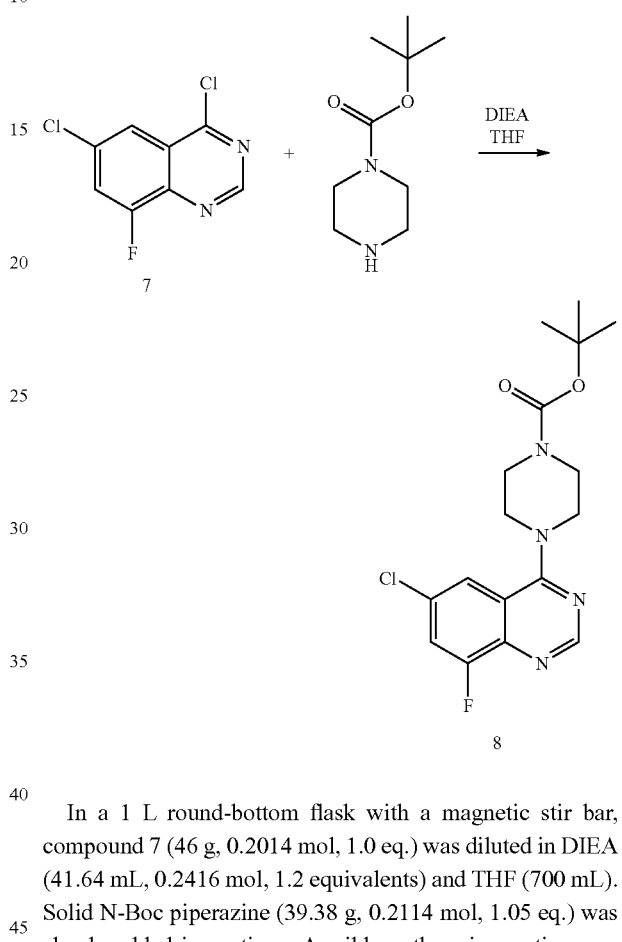

In a 1 L round-bottom flask with a magnetic stir bar, compound 7 (46 g, 0.2014 mol, 1.0 eq.) was diluted in DIEA (41.64 mL, 0.2416 mol, 1.2 equivalents) and THF (700 mL). Solid N-Boc piperazine (39.38 g, 0.2114 mol, 1.05 eq.) was slowly added in portions. A mild exothermic reaction was observed. The reaction mixture was allowed to stir at room temperature for 2 hours then was quenched with saturated NaCl solution (100 mL), water (400 mL), and EtOAc (500 mL). The layers were separated, and the aqueous layer was extracted with EtOAc (2×200 mL). The combined organic layers were dried (Na$_2$SO$_4$) and concentrated to give a gray solid. The crude solid was stirred in 2:1 TBME/hexanes (300/150 mL) overnight. The solids were filtered then washed with hexane (250 mL) to recover 52 g of impure product. The TBME/hexanes slurry was repeated to recover 46 g (59%) of compound 8. All remaining impure material was combined and purified via silica gel chromatography (4:1 hexane/EtOAc) to recover another 11.2 g (14%) of 8 for a total combined yield of 57.2 g (74%). $^1$H NMR (500 MHz, CDCl$_3$) δ 8.77 (s, 1H), 7.64 (t, J=1.8 Hz, 1H), 7.46 (dd, J=9.4, 2.2 Hz, 1H), 3.79-3.74 (m, 4H), 3.67-3.63 (m, 4H), 1.50 (s, 9H).

Example 7

Synthesis of 1-((3R)-4-(6-chloro-8-fluoro-7-(2-fluoro-6-hydroxyphenyl)quinazolin-4-yl)-3-methyl-piperazin-1-yl)prop-2-en-1-one

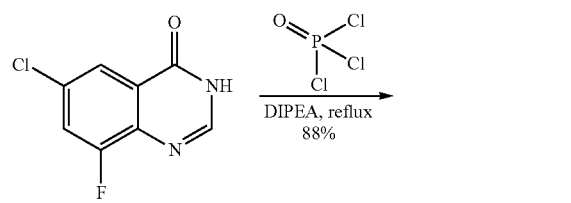

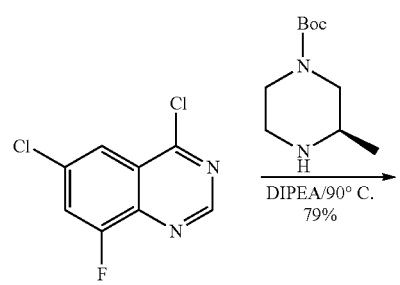

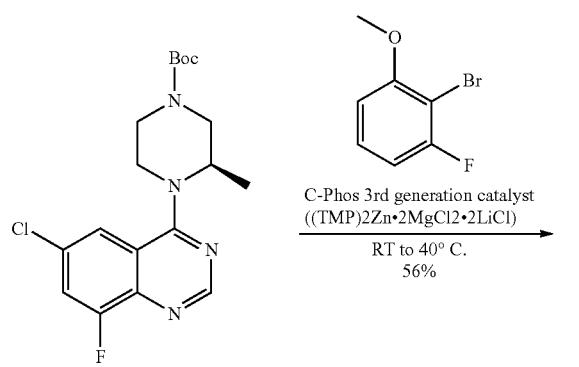

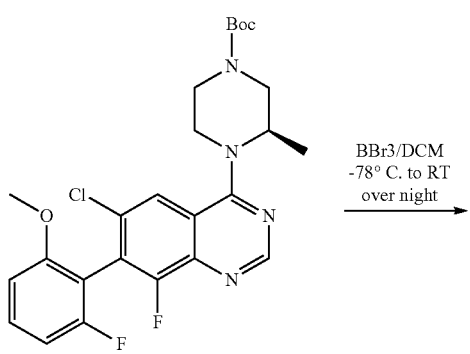

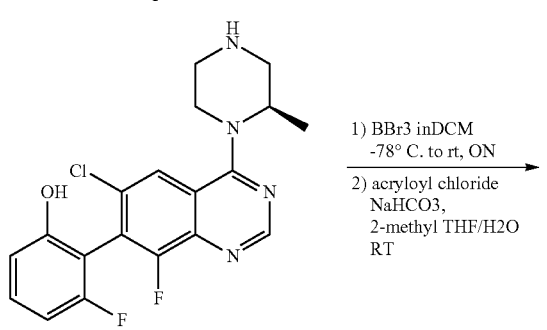

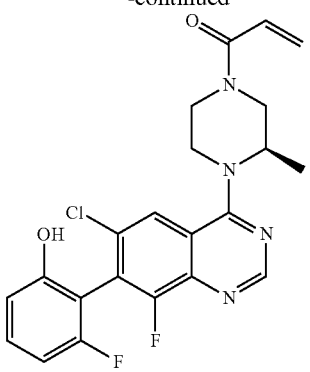

Compound 66
61% in two steps

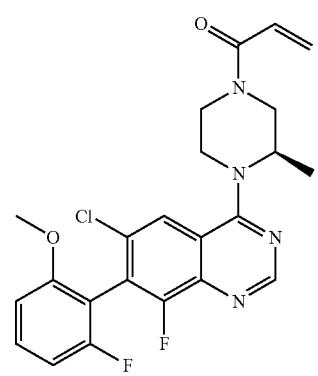

Compound 67
36%

Compounds 66 and 67 were prepared as illustrated above and according to the general procedures described in Examples 1-6.

Example 8

Synthesis of 1-(4-(6-chloro-8-fluoro-7-(2-fluoro-6-hydroxyphenyl)quinazolin-4-yl)-3,3-dimethylpiperazin-1-yl)prop-2-en-1-one

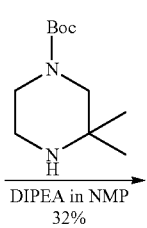

77
-continued

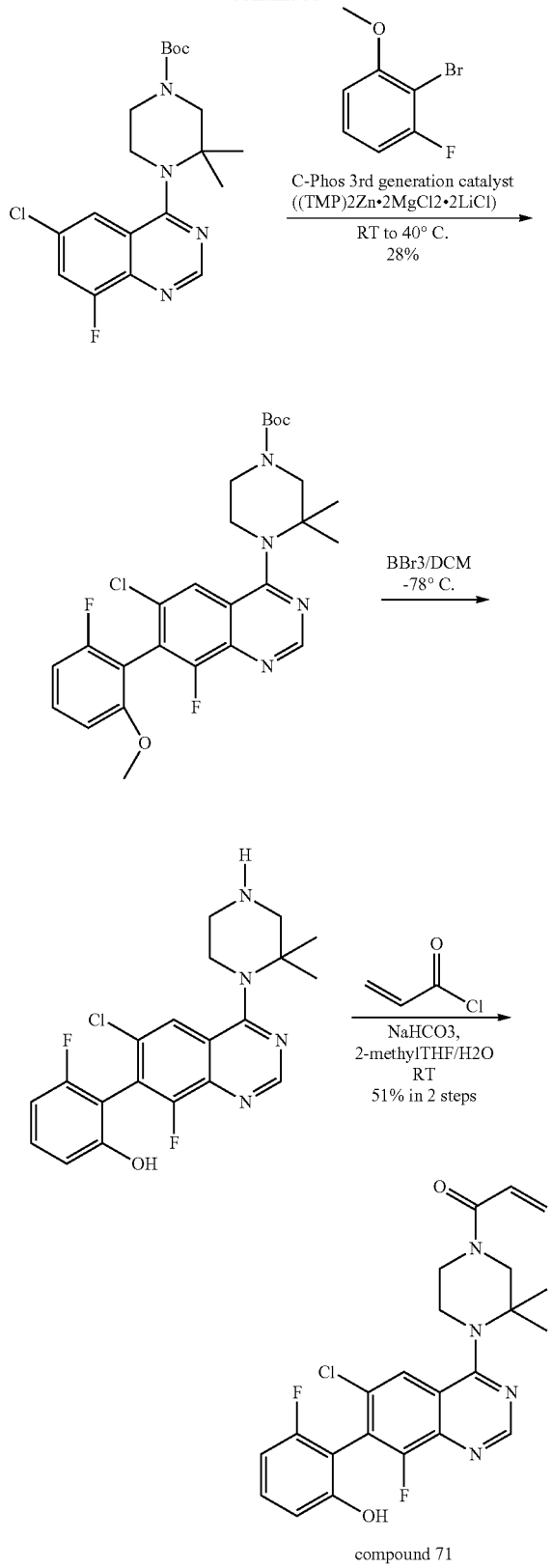

Compound 71 was prepared as illustrated above and according to the general procedures described in Examples 1-6.

78

Example 9

Synthesis of 1-((3S)-4-(6-chloro-8-fluoro-7-(2-fluoro-6-hydroxyphenyl)quinazolin-4-yl)-3-methyl-piperazin-1-yl)prop-2-en-1-one

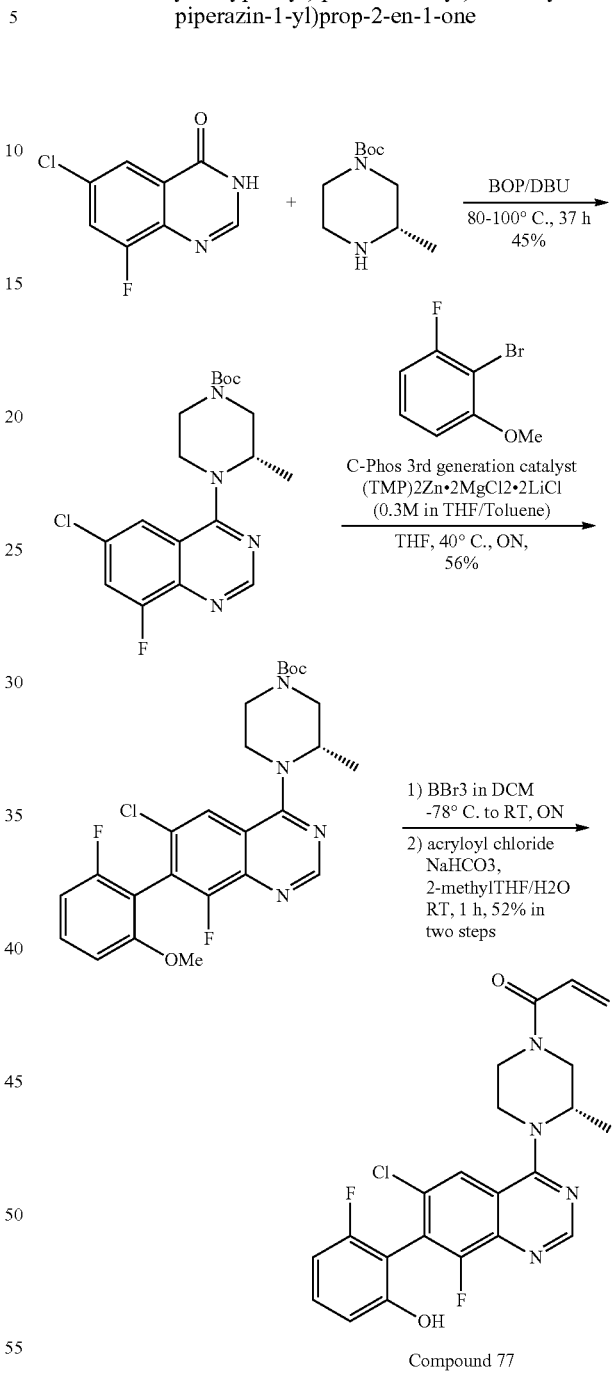

Compound 77 was prepared as illustrated above and described below.

tert-Butyl (S)-4-(6-chloro-8-fluoroquinazolin-4-yl)-3-methylpiperazine-1-carboxylate To a mixture of 800 mg (4.04 mmol, 1.0 eq.) of 6-chloro-8-fluoroquinazolin-4(3H)-one and BOP (1.1 eq.) in acetonitrile, DBU (1.3 eq.) and tert-butyl (S)-3-methylpiperazine-1-carboxylate (1.1 eq.) were added sequentially. The resulting mixture was stirred at 80-100° C. for 37 h. The mixture was cooled down, concentrated in vacuo and then partitioned between water and ethyl acetate. The combined organic layer was washed with brine, dried over anhydrous sodium sulfate, filtered and concentrated in vacuo. The residue was purified by flash column chromatography (stepwise gradient of 0-10% MeOH in dichloromethane) to afford the desired product (685 mg, 45% yield).

tert-Butyl (3S)-4-(6-chloro-8-fluoro-7-(2-fluoro-6-methoxyphenyl)quinazolin-4-yl)-3-methylpiperazine-1-carboxylate A flame dried round bottle (evacuated under vacuum and filled with $N_2$) was fitted with mechanical stirring, and charged with tert-butyl (S)-4-(6-chloro-8-fluoroquinazolin-4-yl)-3-methylpiperazine-1-carboxylate (685 mg, 1.80 mmol, 1.0 eq.) solution in dry THF. Bis(2,2,6,6-tetramethylpiperidinyl)zinc, lithium chloride, magnesium chloride complex (($TMP)_2Zn.2MgCl_2.2LiCl$) (0.35 M solution in THF/toluene, 1.0 eq.) was dropwise added. The reaction was allowed to stir for 45 min at RT and then degassed by bubbling nitrogen through the solution for 15 min. Solid 2-bromo-1-fluoro-3-methoxybenzene (1.0 eq.) and CPhos 3rd generation precatalyst (0.1 eq.) were added, and the resulting mixture was stirred at 40° C. for 16 h. The reaction mixture was concentrated in vacuo, dissolved in ethyl acetate, cooled in an ice bath, and quenched with a 1:1 solution of saturated ammonium chloride and $H_2O$. The layers were separated, and the aqueous layer was extracted with ethyl acetate. The combined organic layer was dried ($Na_2SO_4$), filtered and concentrated in vacuo. The residue was purified by flash column chromatography (stepwise gradient of 20%-30% EtOAc in hexanes) to afford the desired product (504 mg, 56% yield).

1-((3S)-4-(6-Chloro-8-fluoro-7-(2-fluoro-6-hydroxyphenyl)quinazolin-4-yl)-3-methylpiperazin-1-yl)prop-2-en-1-one At −78° C., $BBr_3$ in dichloromethane (1M, 6.0 eq.) was dropwise added into tert-butyl (3S)-4-(6-chloro-8-fluoro-7-(2-fluoro-6-methoxyphenyl)quinazolin-4-yl)-3-methylpiperazine-1-carboxylate (228 mg, 0.45 mmol, 1.0 eq.) solution in dichloromethane. After addition was complete, the reaction was warmed to RT, and the suspension was stirred for 19 h. The reaction was cooled to 0° C. and quenched with an ice/water. Additional water was added and the layers were separated. The water layer was collected. The organic layer was extracted with water. The combined water layer was concentrated, added 2-MeTHF and solid $NaHCO_3$ (20.0 eq.). The reaction mixture was allowed to stir for 5 min. The acryloyl chloride (2.5 eq.) was added at RT and the resulting mixture was stirred at RT for 1 h. Then 5 N NaOH (0.5 mL) was added to quench the reaction, followed by adding 1 mL of 1 N HCl for neutralization. The organic layer was separated and the aqueous layer was extracted with ethyl acetate. The combined organic layer was washed with brine, dried over anhydrous $Na_2SO_4$, and concentrated in vacuo. The residue was purified by flash column chromatography (stepwise gradient of 0-10% MeOH in dichloromethane) to afford the desired product (104 mg, 52% yield). ESI-MS m/z: 445.1 $[M+H]^+$; $^1H$ NMR (500 MHz, DMSO-d6) δ 10.27 (s, 1H), 8.70 (s, 1H), 7.94 (s, 1H), 7.39-7.34 (q, J=8.5 Hz, 1H), 6.87-6.80 (m, 3H), 6.21-6.16 (m, 1H), 5.43 (dd, J=10, 2.5 Hz, 1H), 4.78 (broad s, 1H), 4.40-3.96 (m, 4H), 3.70-3.61 (m, 2H), 1.30 (s, 3H).

The invention claimed is:

1. A method for preparing a compound having the following structure (I):

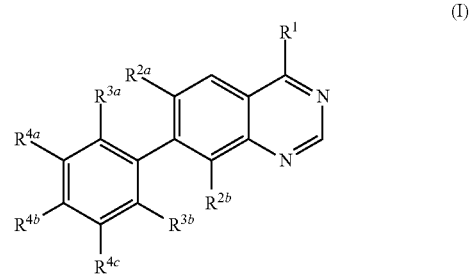

(I)

or a pharmaceutically acceptable salt or stereoisomer thereof, wherein:
$R^1$ is a non-hydrogen substituent;
$R^{2a}$ and $R^{2b}$ are each independently halo, hydroxyl, protected hydroxyl, $C_1$-$C_6$ alkyl, $C_1$-$C_6$ haloalkyl or $C_1$-$C_6$ alkoxy;
$R^{3a}$ and $R^{3b}$ are each independently halo, hydroxyl, protected hydroxyl, $C_1$-$C_6$ alkyl, $C_1$-$C_6$ haloalkyl or $C_1$-$C_6$ alkoxy; or $R^{3a}$ joins with $R^{4a}$ to form a carbocyclyl or heterocyclyl ring, and $R^{3b}$ is halo, hydroxyl, protected hydroxyl, $C_1$-$C_6$ alkyl, $C_1$-$C_6$ haloalkyl or $C_1$-$C_6$ alkoxy; and
$R^{4a}$, $R^{4b}$ and $R^{4c}$ are each independently H or a non-hydrogen substituent; or $R^{4a}$ joins with $R^{3a}$ to form a carbocyclyl or heterocyclyl ring, and $R^{4b}$ and $R^{4c}$ are each independently H or a non-hydrogen substituent;
wherein the method comprises preparing a mixture comprising a compound of structure (II) and a compound of structure (III), the compounds of structure (II) and (III) having the following structures, respectively:

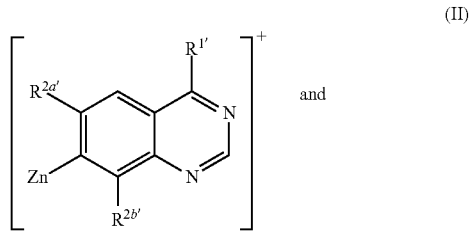

(II)

and

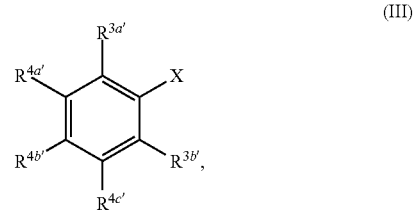

(III)

or a salt thereof, wherein:
$R^{1'}$ is a non-hydrogen, non-acidic substituent;
$R^{2a'}$ and $R^{2b'}$ are each independently halo, protected hydroxyl, $C_1$-$C_6$ alkyl, $C_1$-$C_6$ haloalkyl or $C_1$-$C_6$ alkoxy;
$R^{3a'}$ and $R^{3b'}$ are each independently halo, protected hydroxyl, $C_1$-$C_6$ alkyl, $C_1$-$C_6$ haloalkyl or $C_1$-$C_6$ alkoxy; or $R^{3a'}$ joins with $R^{4a'}$ to form a carbocyclyl or heterocyclyl ring, and $R^{3b'}$ is halo, protected hydroxyl, $C_1$-$C_6$ alkyl, $C_1$-$C_6$ haloalkyl or $C_1$-$C_6$ alkoxy;

$R^{4a'}$, $R^{4b'}$ and $R^{4c'}$ are each independently H or a non-hydrogen substituent; or $R^{4a'}$ joins with $R^{3a'}$ to form a carbocyclyl or heterocyclyl ring, and $R^{4b'}$ and $R^{4c'}$ are each independently H or a non-hydrogen substituent; and X is a leaving group, thereby forming a carbon-carbon bond between the carbon bearing the Zn moiety on compound (II) and the carbon bearing the X moiety on compound (III).

2. The method of claim 1, wherein the compound of structure (II) is prepared by reaction of a mixed-metal, heterocyclyl base with a compound having the following structure (IV):

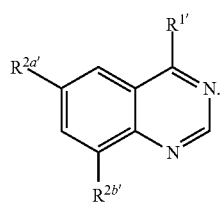

(IV)

3. The method of claim 2, wherein the mixed metal, heterocyclyl base comprises Zn, Mg and Li.

4. The method of claim 2, wherein the mixed metal, heterocyclyl base comprises a piperidinyl heterocycle.

5. The method of claim 2, wherein the mixed metal, heterocyclyl base comprises a 2,2,6,6-Bis(tetramethylpiperidine)zinc, magnesium chloride, lithium chloride complex ((tmp)$_2$Zn.2MgCl$_2$.2LiCl).

6. The method of claim 1, wherein the mixture comprising a compound of structure (II) and a compound of structure (III) further comprises a metal catalyst or metal precatalyst.

7. The method of claim 6, wherein the metal is palladium.

8. The method of claim 7, wherein the metal precatalyst is CPhos 3$^{rd}$ generation.

9. The method of claim 1, wherein the mixture comprising a compound of structure (II) and a compound of structure (III) comprises a polar, aprotic solvent.

10. The method of claim 9, wherein the solvent is tetrahydrofuran.

11. The method of claim 1, wherein $R^1$ and $R^{1'}$ are each independently $C_1$-$C_6$ alkyl, carbocyclyl or heterocyclyl.

12. The method of claim 11, wherein $R^1$ and $R^{1'}$ are each independently heterocyclyl.

13. The method of claim 12, wherein heterocyclyl is piperazinyl.

14. The method of claim 1, wherein $R^1$ and $R^{1'}$ each have the following structure:

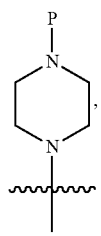

wherein P is a nitrogen protecting group.

15. The method of claim 14, wherein P is butyloxycarbonyl (Boc).

16. The method of claim 1, wherein $R^{2a}$ and $R^{2b}$ are each independently halo.

17. The method of claim 1, wherein $R^{2a'}$ and $R^{2b'}$ are each independently halo.

18. The method of claim 1, wherein $R^{3a}$ and $R^{3b}$ are each independently halo, hydroxyl or $C_1$-$C_6$ alkoxy.

19. The method of claim 1, wherein $R^{3a'}$ and $R^{3b'}$ are each independently halo or $C_1$-$C_6$ alkoxy.

20. The method of claim 1, wherein $R^{4a}$, $R^{4b}$ and $R^{4c}$ are each independently H.

21. The method of claim 1, wherein $R^{4a'}$, $R^{4b'}$ and $R^{4c'}$ are each independently H.

22. The method of claim 1, wherein X is halo.

23. The method of claim 22, wherein halo is bromo.

24. The method of claim 1, wherein the compound of structure (II) has one of the following structures:

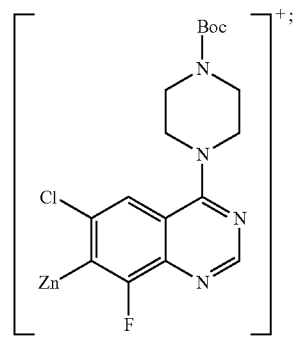

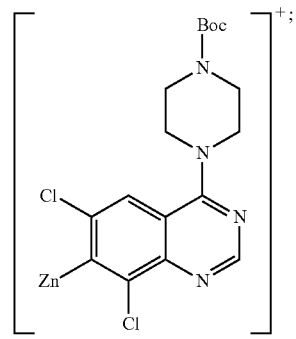

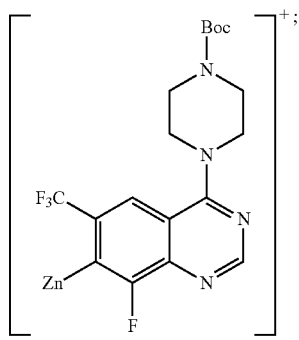

25. The method of claim 1, wherein the compound of structure (III) has one of the following structures:
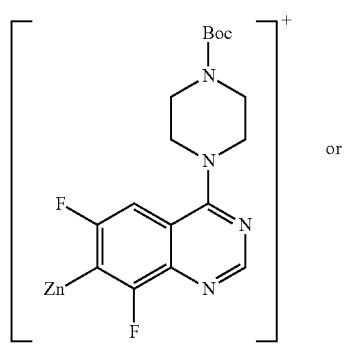
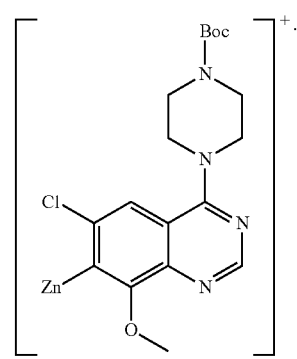
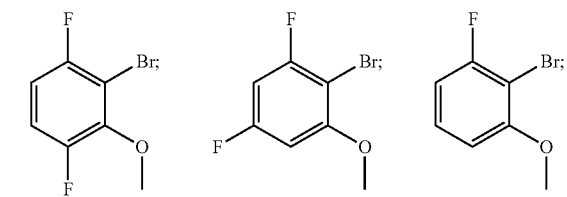
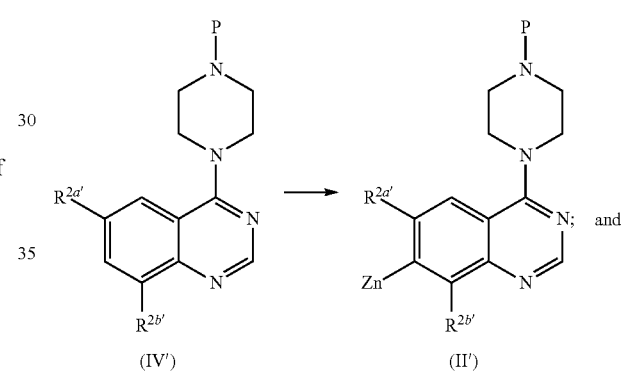
wherein P¹ is nitrogen protecting group.
26. The method of claim 1, comprising the following steps (a) and (b):
(a)
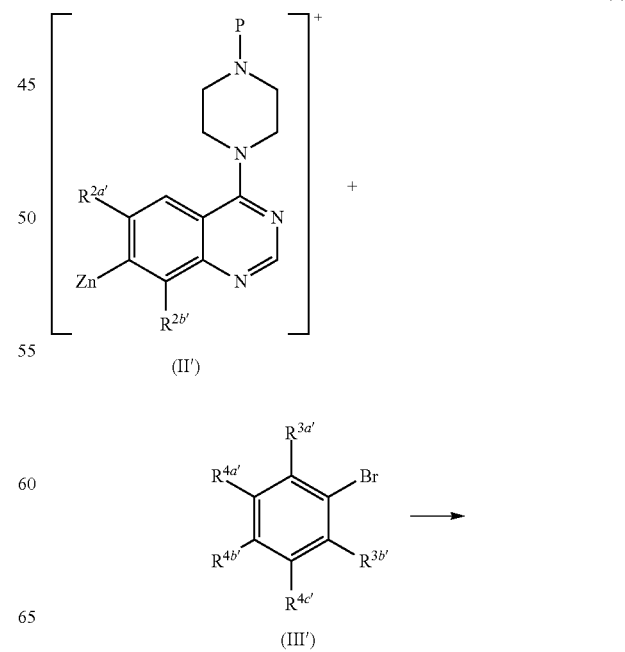
(b)
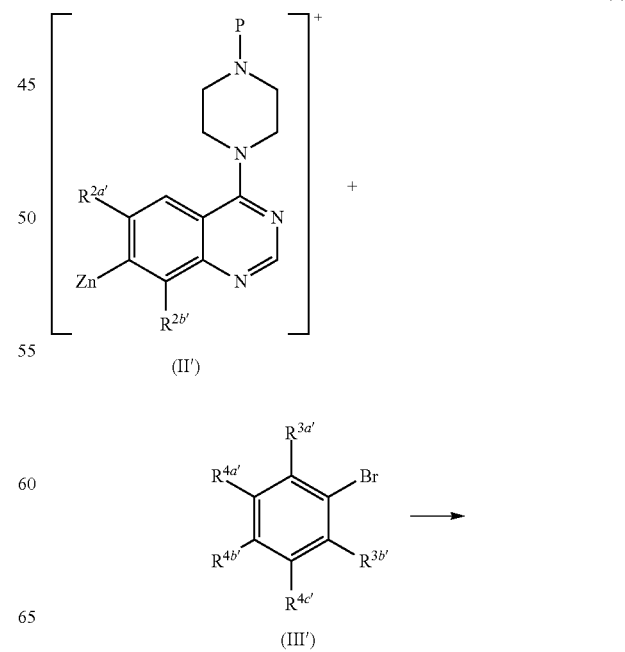

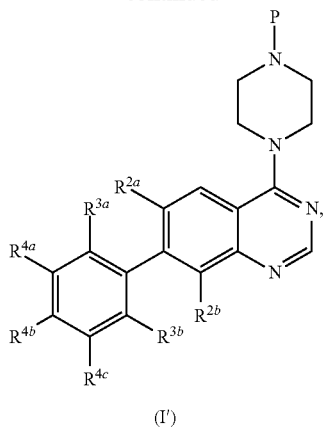

(I')

wherein:
R$^{2a}$, R$^{2b}$, R$^{2a'}$ and R$^{2b'}$ are each independently halo;
R$^{3a}$, R$^{3b}$, R$^{3a'}$ and R$^{3b'}$ are each independently halo, protected hydroxyl or C$_1$-C$_6$ alkoxy; and
R$^{4a}$, R$^{4b}$, R$^{4c}$, R$^{4a'}$, R$^{4b'}$ and R$^{4c'}$ are each independently H.

27. The method of claim 26, wherein P is butyloxycarbonyl.

28. The method of claim 26, wherein R$^{2a}$, R$^{2b}$, R$^{2a'}$ and R$^{2b'}$ are each independently chloro or fluoro.

29. The method of claim 26, wherein R$^{2a}$ and R$^{2b'}$ are each chloro, and R$^{2b}$ and R$^{2b'}$ are each fluoro.

30. The method of claim 26, wherein R$^{3a}$, R$^{3b}$R$^{3a'}$ and R$^{3b'}$ are each independently halo or C$_1$-C$_6$ alkoxy.

31. The method of claim 30, wherein halo is fluoro and C$_1$-C$_6$ alkoxy is methoxy.

32. The method of claim 31, wherein R$^{3a}$ and R$^{3a'}$ are each fluoro, and R$^{3b}$ and R$^{3b'}$ are each methoxy.

* * * * *